US008435493B2

(12) United States Patent
Goodman

(10) Patent No.: US 8,435,493 B2
(45) Date of Patent: *May 7, 2013

(54) IMAGING AGENTS

(75) Inventor: Mark M. Goodman, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/946,027

(22) Filed: Nov. 15, 2010

(65) Prior Publication Data

US 2011/0144483 A1 Jun. 16, 2011

Related U.S. Application Data

(63) Continuation of application No. 11/425,078, filed on Jun. 19, 2006, now Pat. No. 7,837,982.

(60) Provisional application No. 60/693,385, filed on Jun. 23, 2005, provisional application No. 60/728,082, filed on Oct. 19, 2005.

(51) Int. Cl.
*A61K 51/00* (2006.01)
*A61M 36/14* (2006.01)

(52) U.S. Cl.
USPC ....... 424/1.89; 424/1.11; 424/1.65; 424/1.81; 424/1.85

(58) Field of Classification Search ................. 424/1.11, 424/1.65, 1.69, 1.81, 1.85, 1.89, 9.1; 548/100, 548/146, 200, 215, 950; 530/300
See application file for complete search history.

(56) References Cited

U.S. PATENT DOCUMENTS

| 3,855,208 | A | 12/1974 | Rutner et al. |
| 4,325,961 | A | 4/1982 | Kollonitsch et al. |
| 4,358,434 | A | 11/1982 | Tzodikov et al. |
| 4,390,517 | A | 6/1983 | O'Brien et al. |
| 4,483,870 | A | 11/1984 | Kollonitsch et al. |
| 4,695,588 | A | 9/1987 | Kollonitsch et al. |
| 4,743,691 | A | 5/1988 | Bey et al. |
| 4,760,091 | A | 7/1988 | Carson et al. |
| 4,942,231 | A | 7/1990 | Mertens |
| 5,227,467 | A | 7/1993 | Durette et al. |
| 5,279,812 | A | 1/1994 | Krstenansky et al. |
| 5,310,912 | A | 5/1994 | Neumeyer et al. |
| 5,324,504 | A | 6/1994 | Roger, Jr. et al. |
| 5,413,779 | A | 5/1995 | Kuhar et al. |
| 5,637,759 | A | 6/1997 | Hearst et al. |
| 5,698,179 | A | 12/1997 | Neumeyer et al. |
| 5,773,614 | A | 6/1998 | Godfrey et al. |
| 5,808,146 | A | 9/1998 | Goodman et al. |
| 5,817,776 | A | 10/1998 | Goodman et al. |
| 5,853,696 | A | 12/1998 | Elmaleh et al. |
| 6,096,874 | A | 8/2000 | Wallace et al. |
| 6,245,326 | B1 | 6/2001 | Topping et al. |
| 6,344,179 | B1 | 2/2002 | Goodman |
| 6,399,042 | B1 | 6/2002 | Goodman |
| 7,544,715 | B2 | 6/2009 | Goodman |
| 7,837,982 | B2* | 11/2010 | Goodman ............. 424/1.89 |
| 2002/0099184 | A1 | 7/2002 | Goodman |
| 2005/0085545 | A1 | 4/2005 | Susacca et al. |
| 2005/0130274 | A1 | 6/2005 | O'Hagan et al. |
| 2005/0159790 | A1 | 7/2005 | Shalev |
| 2005/0192458 | A1 | 9/2005 | Goodman et al. |
| 2005/0197350 | A1 | 9/2005 | Sekiguchi et al. |
| 2005/0226776 | A1 | 10/2005 | Brandy et al. |
| 2006/0292073 | A1 | 12/2006 | Goodman et al. |
| 2007/0082879 | A1 | 4/2007 | Goodman et al. |
| 2011/0033382 | A1 | 2/2011 | Goodman |

FOREIGN PATENT DOCUMENTS

| EP | 1 464 335 | 10/2004 |
| EP | 06785072 | 5/2009 |
| WO | WO 97/17092 | 5/1997 |
| WO | WO 99/01149 | 1/1999 |
| WO | WO 02/00209 | 1/2002 |
| WO | WO 97/43285 | 11/2002 |

(Continued)

OTHER PUBLICATIONS

Alexoff et al. (1992) "Ion Chromatographic Analysis of High Specific Activity $^{18}$FDG Preparations and Detection of the Chemical Impurity 2-Deoxy-2-chloro-D-Glucose," *Int. J. Rad. Instr. Part. A* 43(11):1313-1322.
Berge et al. (1977) "Pharmaceutical Salts," *J. Pharm. Sci.* 66:1-19.
Bergmann et al. (1962) "Organic Fluorine Compounds Part XXVII. Fluorinated α-Aminoisobutyric Acids," *J. Chem. Soc.* :3462-3463.
Betz et al. (1978) "Polarity of the Blood-Brain Barrier: Neutral Amino Acid Transport into Isolated Brain Capillaries," *Science* 202:225-227.
Bey et al. (1979) "Direct Synthesis of Alpha-Halogenomethyl-Alpha-Amino Acids from the Parent Alpha-Amino Acids," *J. Org. Chem.* 44:15:2732-2742.

(Continued)

*Primary Examiner* — D L Jones
(74) *Attorney, Agent, or Firm* — Emory Patent Group; James C. Mason; Susanne Hollinger

(57) ABSTRACT

The present invention provides novel amino acid compounds useful in detecting and evaluating brain and body tumors. These compounds have the advantageous properties of rapid uptake and prolonged retention in tumors and can be labeled with halogen isotopes such as fluorine-18, iodine-123, iodine-124, iodine-125, iodine-131, bromine-75, bromine-76, bromine-77, bromine-82, astatine-210, astatine-211, and other astatine isotopes. These compounds can also be labeled with technetium and rhenium isotopes using known chelation complexes. The compounds disclosed herein bind tumor tissues in vivo with high specificity and selectivity when administered to a subject. Preferred compounds show a target to non-target ratio of at least 2:1, are stable in vivo and substantially localized to target within 1 hour after administration. Preferred compounds include 1-amino-2-[$^{18}$F]fluorocyclobutyl-1-carboxylic acid (2-[$^{18}$F]FACBC) and 1-amino-2-[$^{18}$F]fluoromethylcyclobutyl-1-carboxylic acid (2-[$^{18}$F] FMACBC). The labeled amino acid compounds of the invention are useful as imaging agents in detecting and/or monitoring tumors in a subject by PET or SPECT.

9 Claims, No Drawings

FOREIGN PATENT DOCUMENTS

| | | |
|---|---|---|
| WO | WO 03/078358 | 9/2003 |
| WO | WO 03/093412 | 11/2003 |
| WO | WO 2004/056725 | 7/2004 |
| WO | WO 2005/021485 | 3/2005 |
| WO | WO 2005/030025 | 4/2005 |
| WO | WO 2005/030677 | 4/2005 |
| WO | WO 2005/051384 | 6/2005 |
| WO | WO 2005/061110 | 7/2005 |
| WO | 2007001940 | 4/2007 |

OTHER PUBLICATIONS

Blough et al. (1996) "Synthesis and Transporter Binding Properties of 3β-(4'-Alkyl-, 4'A;kenyl-, and 4'Alkynylphenyl)nortropane-2β-Carboxylic Acid Methyl Esters: Serotonin Transporter Selective Analogs," *J. Med. Chem.* 39(20):4027-4035.

Blough et al. (1997) "3β-(4-Ethyl-3-iodophenyl)nortropane-2β-carboxylic Acid Methyl Ester as a High-Affinity Selective Ligand for the Serotonin Transporter" *J. Med. Chem.* 40(24):3861-3864.

Bodsch et al. (1988) "Biochemical and Autoradiographic Study of Cerebral Protein Synthesis Fluorine-18 Fluorophenylalanine and Carbon-14 Fluorophenylalanine," *J. Neurochem.* 50(3):979-983, (1988).

Boger et al. (1992) "Functional Analogs of CC-1065 and the Duocarmycins Incorporating the 9a-(chloorormethyl_-1,2,9,9a-tetrahydrocyclopropa[c]benz[e]indol-4-one ($C_2$ 2BI) Alkylation Subunit: Synthesis and Preliminary DNA Alylaation Studies," *J. Am. Chem. Soc.* 114:9318-9327.

Buonocore, E (1992) "Comparison of PET with Conventional Imaging Techniques," *Clinical Positron Emission Tomography*, Mosby-Year Book Inc. St. Louis, MO, pp. 17-22.

Bussolati et al. (1996) "The Stimulation of Na, K, Cl Cotransport and of System A for Neutral Amino Acid Transport is a Mechanism for Cell Colume Increase During the Cell Cycle," *FASB J.* 10:920-926.

Chiotellis et al. (1977) "Preparation of Tc-99m Labeled Pyridoxal-Amino-Acid Complexes and Their Ecaluation," *Int. J. Nuc. Med. Biol.* 4(1):29-41 and CA 1977:498177.

Christensen et al. (1983) "Synthesis and Transport Applications of 3-Aminobicuclo[3.2.1]Octane-3-carboxylic Acids," *J. Med. Chem.* 16:1374-1378.

Christensen et al. (Sep. 1965) "The Use of N-Methylation to Direct the Route of Mediated Transport of Amino Acids," *J. Biol. Chem.* 240(9):3609-3616.

Coleman, RE. (1991) "Single Photon Emission Computed Tomography and Positron Emission Tomography in Cancer Imaging," *Cancer* 67(4 supp.):1261-1270.

Conti et al. (1986) "Tumor Imaging with Carbon-11 Labeled Alpha-Aminoisobutyric Acid (AIB) in a Patient with Advances Malignant Melanoma," *Eur. J. Nuc. Med.* 12:353-356.

Conti, PS (1995) "Introduction to Imaging Brain Tumor Metabolism with Positron Emission Tomography (PET)," *Cancer Invest.* 13(2):244-259.

Conti et al. (1985) "Tumor Localization of Alpha-Aminoisobutyric Acid (AIB) in Human Melanoma Heterotransplants," *Eur. J. Nuc. Med.* 10:45-47.

Damhaut et al. (1997) "No-Carrier-Added Asymmetric Synthesis of Alpha-Methyl-Alpha-Amino Acids Labelled with Fluorine-18," *Tetrahedron* 53(16):5785-5796.

Di Chiro et al. (1982) "Glucose Utilization of Cerebral Gliomas Measured y [$^{18}$F] Fluorodeoxyglucose and Positron Emission Tomography," *Neurology* 32:1323-1329.

Dunzendorfer et al. (1981) "Synthesis and Body Distribution of Alpha-Aminoisobutyric Acid-L-$^{11}$C in Normal and Prostate Cancer-Bearing Rat After Chemotherapy," *Eur. J. Nuc. Med.* 6:535-538.

Dutta et al. (1996) "Structure-Activity Relationship Studies of Novel 4-[2-[Bis(4-fluorophenyl)methoxy]ethyl]-1-(3-phenylpropyl-piperidine) Analogs: Synthesis and Biological Evaluation at the Dopamine and Serotonin Transporter Sites," *J. Med. Chem.* 39:749-756.

Feinendegen, LE (1993), "Contributions of Nuclear Medicine to the Therapy of Malignant Tumors (editorial)," *J. Can. Res. Clin. Oncol.* 119(6):320-322, (1993).

Finar (1973) *Organic Chemistry, vol. 1, The Fundamental Principles*, $6^{th}$ ed., pp. 61-62.

Fishman et al. "SPECT Imaging of Dopamine Transporter Sites in Normal and MPTP-Treated Rhesus Monkeys" (1997) *J. Nucl. Med.* 38:144-150.

Giros et al. (1996) "Hyperlocomotion and Indifference to Cocaine and Amphetamine in Mice Lacking the Dopamine Transporter" *Nature* 379:606-612.

Goodman et al. (1994) "Synthesis and Characterization of Radioiodinated N-(3-lodopropen-1-yl)-2β-carbomethoxy-3β-(4-chlorophenyl)tropanes: Potential Dopamine Reuptake Site Imaging Agents" *J. Med. Chem* 37:1535-1542.

Goodman et al. (1992) "Automated Synthesis of Radiotracers for PET Applications" In; *Clinical Positron Emission Tomography*, Hubner et al. Eds., Mosby Yearbook, Ch. 14 , pp. 110-122.

Goodman et al. (1997) "Initial Evaluation of High Energy NaI-Based Coincidence Brain Imaging of Tumor Amino Acid Uptake and Striatal Dopamine Transporters with [F-19] FACBC and [F-18] FECNT," *J. Nuc. Med.* 38(5):152p-153p (No. 619).

Griffeth et al. (1993) "Brain Metastases from Non-Central Nervous System Tumors: Evaluation with PET," *Radiology* 186:37-44.

Heindel et al. (1977) "99mTc-1-Aminocyclopentane Carboxylic cid: Tumor and Tissue Distribution Results on a Labeled Cytotoxic Amino Acid," *Int. J. Appl. Radiat. Iso.* 27(11):621-625 as Abstracted in CA 1977:167194.

Hoyte et al. (1970) "Fluorine-18 Labeled Amino-Acids for Organic Imaging," *J. Nuc. Med.* 11(10):633.

Hume et al. "Citalopram: Labeling with Carbon-11 and Evaluation in Rat as a Potential Radioligand for in Vivo PET Studies of 5-HT Re-uptake Sites" (1991) *Nucl. Med. Biol.* 18:339-351.

International Search Report, Corresponding to International Application No. PCT/US06/23740, Mailed Mar. 22, 2007.

International Search Report, Corresponding to International Application No. PCT/US96/18455, Mailed Mar. 7, 1997.

International Search Report, Corresponding to International Application No. PCT/US03/12748, Mailed Nov. 5, 2003.

International Search Report, Corresponding to International Application No. PCT/US06/23699, Mailed Apr. 5, 2007.

Ishiwata et al. (1993) "Re-evaluation of Amino Acid PET Studies: Can the Protein Synthesis Rates in Brain and Tumor Tissues be Measured in Vivo," *J. Nucl. Med.* 34(11):1936-1943.

Iwata et al. (May 2003) "Radiosynthesis of O-[11C]methyl-L-tyrosine and O[18F]Fluoromethyl-L-tyrosine as Potential PET Tracers for Imaging Amino Acid Transport," *J. Labelled Compnd. Radiopharm.* 46(6):555-566.

Jager et al. (2001) "Radiolabeled Amino Acids: Basic Aspects and Clinical Applications in Oncology," *J. Nuc. Med.* 42:432-445.

Kilbourn et al. (1989) "Synthesis of Radiolabeled Inhibitors of Presynaptic Monoamine Uptake Systems: [$^{18}$F]GBR 13119(DA),[$^{11}$C]Nisoxetine (NE), and [$^{11}$C]Fluoxtine (5-HT)" *J. Label. Compd. Radiopharm.* 26:412-414. (Symposium Abstract).

Kollonitsch et al. (1975) "Selective Fluorination of Hydroxy Amines and Hydroxy Amino-Acids with Sulfur Tetra Fluoride in Liquid Hydrogen Fluoride" *J. Org. Chem.* 40(25):3808-3809.

Kubota et al. (1984) "Tumor Detection with Carbon-11-Labelled Amino Acids," *Eur. J. Nuc. Med.* 9:136-140.

Kung et al (1995). "IPT: A Novel Iodinated Ligand for the CNS Dopamine Transporter" (1995) *Synapse* 20:316-324.

Kuntschke et al. (1995) "New [$^{99m}$Tc]-Cytetrene Amine Compounds as Specific Brain Imaging Agents," *J. Labelled Comp. Radiopharm.* 36(2):193-203.

Langleben et al. (2000) "PET in Differentiation of Recurrent Brain Tumor from Radiation Injury," *J. Nuc. Med.* 41:1861-1867.

Laverman et al. (2002) "Fluorinated Amino Acids for Tumor Imaging with Positron Emission Tomography," *Eur. J. Nuc. Med.* 29(5):681-690.

Liu et al. (1996) "Labeling Cyclic Glycoprotein IIb/IIIa Receptor Antagonists with $^{99m}$Tc by the Preformed Chelate Approach: Effects of Chelators on Properties of [$^{99m}$Tc] Chelator-Peptide Conjugates," *Bioconjug. Chem.* 7(2):196-202.

Malison et al. (1995) "Striatal Dopamine Transporter Imaging in Nonhuman primates with Iodine-123-IPT SPECT" *J. Nucl. Med.* 36:2290-2297.

Martarello et al. (2001) "Synthesis and Biological Evaluation of Syn and Anti FMACBC, New Amino Acids for Tumor Imaging with PET," *J. Labelled Compd. Radiopharm.* 44:S385-S387.

Martarello et al. (2002) "Synthesis of *Syn*- and *Anti*-1-Amino-3-[$^{18}$F]Fluoromethyl-Cyclobutane-1-Carboxylic Acid (FMACBC), Potential PET Ligands for Tumor Detection," *J. Med. Chem.* 45(11):2250-2259.

Maryanoff et al. (1987) "Pyrroloisoquinoline Antidepressants. In-Depth Exploration of Structure-Activity Relationships" *J. Med. Chem.* 30:1433-1454.

Mathis et al. (1993) "Synthesis and Biological Evaluation of a PET Radioligand for Serotonin Uptake Sites: [F-18]5-Fluoro-6-Nitroquipazine" *J. Nucl. Med.* 34:7P-8P.

Matsushima et al. (1984) "Evaluation of Technetium-99m-Labeled Amino Acids as Radiopharmaceuticals. VI. N-Pyridoxylidenehydrazine-N',N'-Diacetic Acid," *Chem. Pharm. Bull.* 32(6):2262-2266.

McConathy et al. (2003) "Improved Synthesis of *Anti*-[$^{18}$F]FACBC: Improved Preparation of Labeling Precursor and Automated Radiosynthesis," *Appl. Rad. Isotopes* 58:657-666.

McConathy et al. (2003) "Synthesis and Evaluation of 2-Amino-4-[$^{18}$F]Fluoro-2-Methylbutanoic Acid (FAMB): Relationship of Amino Acid Transport to Tumor Imaging Properties of Branched Fluorinated Amino Acids," *Nuc. Med. Biol.* 30(5):477-490.

McConathy et al. (2001) "Famp and N-methyl famp: Fluorinated analogs of aminoisobutyric acid with high uptake in a rodent model of intracranial tumors," 48$^{th}$ Annual Meeting of the Society of Nuclear Medicine, Toronto, Canada, Jun. 23-27, 2001, Abstract No. 558.

McConathy et al. (2001) "Introduction of $^{18}$F at neopentyl positions via cyclic sulfamidates: Synthesis of $^{18}$F-labeled α,α-dialkyl amino acids as potential tumor imaging agents," J Labelled Cpd. Radiopharm. 44(Suppl. 1):S376-S378.

Meegalla et al. (1997) "Synthesis and Characterization of Technetium-99m-Labeled Tropanes as Dopamine Transporter-Imaging Agents," *J. Med. Chem.* 40:9-17.

Monclus et al. (1995) "Asymmetric Synthesis of Fluorinated L-Tyrosine and Meta-L-Tyrosines," *J. Fluorine Chem.* 70(1)39-43.

Murphy et al. (1986) "Use of Serotonergic Agents in the Clinical Assessment of Central Serotonin Function" *J. Clin. Psychiatr.* 47(supp)9-15.

Nagren et al. (2000) "[N-methyl-$^{11}$C]MeAIB, A Tracer for System A Amino Acid Transport: Preparation from [$^{11}$C]Methyl Triflate and HPLC Metabolite Analysis of Plasma Samples After Intravenous Administration in Man," *J. Labelled Cpd Radiopharm.* 43:1013-1021.

Niznik et al. (1991) "The Dopamine Transporter is Absent in Parkinsonian Putamen and Reduced in the Caudate Nucleus" *J. Neurochem.* 56:192-198.

Ogawa et al. (1993) "Cerebral Glioma: Evaluation with Methionine PET$^1$," *Radiology* 186:45-53.

Ogura et al. (1984) "A Versatile Synthesis of Four-, Five, and Six-Membered Cyclic Ketones Using Methyl Methylthiomethyl Sulfoxide," *Bull. Chem. Soc. Jpn.* 57:1637-1642.

Palacin et al. (1998) "Molecular Biology of Mammalian Plasma Membrane Amino Acid Transporters," *Physiol. Rev.* 78:969-1054.

Posakony et al. (1999) "Progress in the Synthesis of [18-F]-Fluoroamines; Precursors to β-Selective Andrenergic Ligands," *J. Label. Comp. Radiopharm.* 42:S527-S529.

Schmall et al. (1987) "Imaging Studies of Patients with Malignant Fibrous Histiocytoma using C-11-Alpha-Aminoisobutyric Acid (AIB)," *Clin. Nucl. Med* 12(1):22-26.

Schober et al. (1992) "Evaluation of Brain Tumors by Positron Emission Tomography," *Radiologe* 32(6):283-289.

Shiba et al. (1984) "Comparative Distribution Study of Carbon-14-Labeled Amino-Acids Glucose Analog and Precursor of Nucleic-Acid as Tumor Seeking Agents," *Radioisotopes* 33(8):526-532.

Shotwell et al. (1983) "The Regulation of Neutral Amino Acid Transport in Mammalian Cells," *Biochem. Biophys. Acta.* 737:267-284.

Shoup et al. (1999) "Synthesis of [F-18]-1-Amino-3-Fluorocyclobutane-1-Carboxylic Acid (FACBC): A PET Tracer for Tumor Detection," *J. Labeled Compounds Radiopharm.* 42(3):215-225.

Shoup et al. (1999) "Synthesis and Evaluation of [$^{18}$F]1-Amino-3-Fluorocyclobutane-1-Carboxylic Acid to Image Brain Tumors," *J. Nuc. Med.* 40(2):331-338.

Shoup et al. (1995) "Synthesis and Evaluation of [18F]1-Amino-3-Fluorocyclo-Butane-1-Carboxylic Acid (FACB) for Tumor Localization," In; *Eleventh International Symposium on Radiopharmaceutical Chemistry*, Abstracts, Vancouver, B.C. Canada, Aug. 13-17, pp. 153-155.

Schuster et al. (May 2003) "Validation of Human Estimated Radiation Dosimetry from Animal Data for the Synthetic PET Amino Acid Radiotracer 1-Amino-3-[F-18]fluorocyclobutane-1-carboxylic acid (F-18-FACBC)," *J. Nuc. Med.* 44(5):322p-323p.

Schuster et al. (May 2003) "Uptake of Synthetic PET Amino Acid radiotracer 1-Amino-3-[F-18]fluorocyclobutane-1-carboxylic Acid (F-18-FACBC) with Primary and Metastic Brain Cancer Compared with 18F0Fluorodeoxyglucose (F-19-FDG)," *J. Nuc. Med.* 44(5):167p.

Suehiro et al. (1991) "Radiosynthesis and Evaluation of *N*-(3-[$^{18}$F]Fluoropropyl) paroxetine as a Radiotracer for in Vivo Labeling of Serotonin Uptake Sites by PET" (1991) *Nucl. Med. Biol.* 18:791-796.

Suehiro et al. (1992) "Synthesis of a Radiotracer for Studying Serotonin Uptake Sites with Positron Emission Tomography: [$^{11}$C]McN-5652-Z" *J. Label Comp. Radiopharm.* 31:841-848.

Suehiro et al. (1993) "A PET Radiotracer for Studying Serotonin Uptake Sites: Carbon-11-McN-5652Z" *J. Nucl. Med.* 34:120-127.

Supplementary European Search Report, Corresponding to European Application No. 03747599.3, Jun. 28, 2007.

Supplementary Partial European Search Report, Corresponding to European Application No. 96 94 2015, Completed May 18, 2001.

Tamemasa et al. (1984) "Tumor Detection with some 99m-Tc-Labeled S-Containing Amino Acids," *Gann.* 75(5):395-402.

Taylor et al. (1983) "Fluorinated Alpha-methylamino Acids as Fluorine-19 NMR Indicators of Intracellular pH," *Biophys. J.* 43(3):261-267.

Taylor et al. (2000) "Generic Models for Radionuclide Dosimetry: $^{11}$C-, $^{18}$F- or $^{75}$Se-Labelled Amino Acids," *Appl. Rad. Isotopes* 52(4):911-922.

Thierry et al. (1998) "2-Phenyl Isopropyl and t-Butyl Trichloroacetimidates: Useful Reagents for Ester Preparation of N-Protected Amino Acids Under Neutral Conditions," *Tetrahedron Lett.* 39:1557-1560.

Uehara et al. (1997) "Imaging Experimental Brain Tumors with 1-Aminocyclopentane Carboxylic Acid and Alpha-Aminoisobutyric Acid: Comparison to Fluorodeoxyglucose and Diethylenetriaminepentaacetic Acid in Morphology Defined Tumor Regions," *J. Cereb. Blood Flow Metab.* 17:1239-1253, (1997).

Verbruggen et al. (1992) "Technetium-99m-L,L,-Ethylenedicystein: A Renal Imaging Agent. I. Labeling and Evaluation in Animals," *J. Nuc. Med.* 33(4):551-557.

Washburn et al. (1979) "1-aminocyclobutane[$^{11}$C]Carboxylic Acid, a Potential Tumor-Seeking Agent," *J. Nuc. Med.* 20:1055-1061.

Washburn et al. (1979) "High-Level Production of C-11-Carboxyl-Labeled Amino Acids," In; *Radiopharmaceuticals II: Proceedings of the 2$^{nd}$ International Symposium on Radiopharmaceuticals*, Mar. 19-22, Seattle, Washington, pp. 767-777.

Weiland et al. (1988) "NMDA Receptor Channels: Labeling of MK-801 with Iodine-125 and Fluorine-18," *Appl. Radiat. Isotop.* 39:1219-1225.

Yu et al. (2003) "Synthesis, in Vitro and in Vivo Characterization of Syn/Anti[123I] IVACBC as Potential Tumor Imaging Agents," *J Labelled Compd. Radiopharm.* 46:S131.

International Search Report, International Application No. PCT/US06/23699, mailed Apr. 5, 2007, 2 pages.

Atkinson, R. S. et al., "Reactions of cyclic beta-keto esters and other enol derivatives with 3-acetoxyamino-2-isopropylquinazolin-4(3H)-one; further oxidation of the cyclic alpha-(3,4-dihydro-2-isopropyl-4-oxoquinazolin-3-yl) amino ketones with lead tetraacetate leading to ring-expansion (in dichloromethane) and ring-cleavage (in methanol)," J Chem Soc, Perkin Trans. 1(12):1533-1542, 1995.

Avenoza, A. et al., "The use of 4-hetaryliden- and 4-arliden-5(4H)-oxazolones as dienophiles. Appropriate reagents for the synthesis of cyclic analogues of natural amino acids," J Heterocyclic Chemistry 34:1099-1110, 1997.

Washburn, L.C. et al., "Effect of structure on tumor specificity of alicyclic alpha-amino acids," Cancer Research 38(8):2271-2273, 1978.

Zitsane, D. R. et al., "Exotic amino acids: I. Synthesis of alpha-amino acids with a cyclohexene substituent," Russian J Organic Chemistry 35(10):1457-1460, 1999.

Jarkas et al., 2010, (R,S)-anti-1-Amino-2-[18F]Fluorocyclopentyl-1-carboxylic Acid: Synthesis from Racemic 2-Benzyloxycyclopentanone and Biological Evaluation for Brain Tumor Imaging with Positron Emission TomographyJ. Med. Chem., 53 (18), pp. 6603-6607.

Savir-Baruch et al (2010) Pilot evaluation of 1-amino-2-[18F]fluorocyclopentane-1-carboxylic acid (anti-2-[18F] FACPC) PET-CT in recurrent prostate carcinoma. J Nucl Med 51(suppl 2):237P.

Savir-Baruch et al., 2011, Pilot Evaluation of Anti-1-amino-2-[18F] fluorocyclopentane-1-carboxylic acid (anti-2-[18F] FACPC) PET-CT in Recurrent Prostate Carcinoma, Mol Imaging Biol. 13(6):1272-7.

* cited by examiner

IMAGING AGENTS

CROSS-REFERENCE TO RELATED APPLICATIONS

This application is a continuation of U.S. patent application 11/425,078, filed Jun. 19, 2006, which claims the benefit of U.S. Provisional Applications No. 60/693,385, filed Jun. 23, 2005 and No. 60/728,082, filed Oct. 19, 2005, all of which are incorporated herein in their entirety to the extent not inconsistent herewith.

ACKNOWLEDGEMENT OF FEDERAL RESEARCH SUPPORT

This invention was made with government support under Grant No. 5-R21-CA-098891 awarded by the National Institutes of Health. The government has certain rights in this invention.

BACKGROUND OF THE INVENTION

This invention relates to novel amino acid analogs having specific and selective binding in a biological system, particularly brain and systemic tumors, and capable of being used for positron emission tomography (PET) and single photon emission (SPECT) imaging methods.

The development of radiolabeled amino acids for use as metabolic tracers to image tumors using positron emission tomography (PET) and single photon emission computed tomography (SPECT) has been underway for some time. Although radiolabeled amino acids have been applied to a variety of tumor types, their application to intracranial tumors has received considerable attention due to potential advantages over other imaging modalities. After surgical resection and/or radiotherapy of brain tumors, conventional imaging methods such as CT and MRI do not reliably distinguish residual or recurring tumor from tissue injury due to the intervention and are not optimal for monitoring the effectiveness of treatment or detecting tumor recurrence [Buonocore, E (1992), *Clinical Positron Emission Tomography*. Mosby-Year Book, Inc. St. Louis, Mo., pp 17-22; Langleben, D D et al. (2000), *J. Nucl. Med.* 41:1861-1867].

The leading PET agent for diagnosis and imaging of neoplasms, 2-[$^{18}$F]fluorodeoxyglucose (FDG), has limitations in the imaging of brain tumors. Normal brain cortical tissue shows high [$^{18}$F]FDG uptake as does inflammatory tissue which can occur after radiation or surgical therapy; these factors can complicate the interpretation of images acquired with [$^{18}$F]FDG [Griffeth, L K et al. (1993), *Radiology*. 186: 37-44; Conti, P S (1995)].

A number of reports indicate that PET and SPECT imaging with radiolabeled amino acids better define tumor boundaries within normal brain than CT or MRI allowing better planning of treatment [Ogawa, T et al. (1993), *Radiology*. 186: 45-53; Jager, P L et al. (2001), *Nucl. Med.*, 42:432-445]. Additionally, some studies suggest that the degree of amino acid uptake correlates with tumor grade, which could provide important prognostic information [Jager, P L et al. (2001) *J. Nucl. Med.* 42:432-445].

Amino acids are required nutrients for proliferating tumor cells. A variety of amino acids containing the positron emitting isotopes carbon-11 and fluorine-18 have been prepared. They have been evaluated for potential use in clinical oncology for tumor imaging in patients with brain and systemic tumors and may have superior characteristics relative to 2-[$^{18}$F]FDG in certain cancers. These amino acid candidates can be subdivided into two major categories. The first category is represented by radiolabeled naturally occurring amino acids such as [$^{11}$C]valine, L-[$^{11}$C]leucine, L-[$^{11}$C]methionine (MET) and L[1-$^{11}$C]tyrosine, and structurally similar analogues such as 2-[$^{18}$F]fluoro-L-tyrosine and 4-[$^{18}$F]fluoro-L-phenylalanine. The movement of these amino acids across tumor cell membranes predominantly occurs by carrier mediated transport by the sodium-independent leucine type "L" amino acid transport system. The increased uptake and prolonged retention of these naturally occurring radiolabeled amino acids into tumors in comparison to normal tissue is due in part to significant and rapid regional incorporation into proteins. Of these radiolabeled amino acids, [$^{11}$C]MET as been most extensively used clinically to detect tumors. Although [$^{11}$C]MET has been found useful in detecting brain and systemic tumors, it is susceptible to in vivo metabolism through multiple pathways, giving rise to numerous radiolabeled metabolites. Thus, graphical analysis with the necessary accuracy for reliable measurement of tumor metabolic activity is not possible. Studies of kinetic analysis of tumor uptake of [$^{11}$C]MET in humans strongly suggest that amino acid transport may provide a more sensitive measurement of tumor cell proliferation than protein synthesis.

The shortcomings associated with [$^{11}$C]MET may be overcome with a second category of amino acids. These are non-natural amino acids such as 1-aminocyclobutane-1-[$^{11}$C]carboxylic acid ([$^{11}$C]ACBC). The advantage of [$^{11}$C]ACBC in comparison to [$^{11}$C]MET is that it is not metabolized. A significant limitation in the application of carbon-11 amino acids for clinical use is the short 20-minute half-life of carbon-11. The 20-minute half-life requires an on-site particle accelerator for production of the carbon-11 amino acid. In addition only a single or relatively few doses can be generated from each batch production of the carbon-11 amino acid. Therefore carbon-11 amino acids are poor candidates for regional distribution for widespread clinical use.

In order to overcome the physical half-life limitation of carbon-11, we have recently focused on the development of several new fluorine-18 labeled non-natural amino acids, some of which have been disclosed in U.S. Pat. Nos. 5,808, 146 and 5,817,776, both of which are incorporated herein by reference. These include anti-1-amino-3-[$^{18}$F]fluorocyclobutyl-1-carboxylic acid (anti-[$^{18}$F]FACBC), syn-1-amino-3-[$^{18}$F]fluorocyclobutyl-1-carboxylic acid (syn-[$^{18}$F]FACBC), syn- and anti-1-amino-3-[$^{18}$F]fluoromethyl-cyclobutane-1-carboxylic acid (syn- and anti-[$^{18}$F]FMACBC). These fluorine-18 amino acids can be used to image brain and systemic tumors in vivo based upon amino acid transport with the imaging technique Positron Emission Tomography (PET). Our development involved fluorine-18 labeled cyclobutyl amino acids that move across tumor capillaries by carrier-mediated transport involving primarily the "L" type large, neutral amino acid and to a lesser extent the "A" type amino acid transport systems. Our preliminary evaluation of cyclobutyl amino acids labeled with positron emitters, which are primarily substrates for the "L" transport system, has shown excellent potential in clinical oncology for tumor imaging in patients with brain and systemic tumors. The primary reasons for proposing $^{18}$F-labeling of cyclobutyl/branched amino acids instead of $^{11}$C ($t_{1/2}$=20 min.) are the substantial logistical and economic benefits gained with using $^{18}$F instead of $^{11}$C-labeled radiopharmaceuticals in clinical applications. The advantage of imaging tumors with $^{18}$F-labeled radiopharmaceuticals in a busy nuclear medicine department is primarily due to the longer half-life of $^{18}$F ($t_{1/2}$=110 min.). The longer half-life of $^{18}$F allows off-site distribution and multiple doses from a single production lot of radio tracer. In addition, these non-metabolized amino acids may also have wider application as imaging agents for certain systemic solid tumors that do not image well with 2-[$^{18}$F] FDG PET. WO 03/093412, which is incorporated herein by reference, further discloses examples of fluorinated analogs of α-aminoisobutyric acid (AIB) such as 2-amino-3-fluoro-2-methylpropanoic acid (FAMP) and 3-fluoro-2-methyl-2-(methylamino)propanoic acid (N-MeFAMP) suitable for labeling with $^{18}$F and use in PET imaging. AIB is a nonmetabolizable α,α-dialkyl amino acid that is actively transported into cells primarily via the A-type amino acid transport system. System A amino acid transport is increased during cell growth and division and has also been shown to be upregulated in tumor cells [Palacín, M et al. (1998), Physiol. Rev. 78: 969-1054; Bussolati, O et al. (1996), FASEB J. 10:920-926]. Studies of experimentally induced tumors in animals and spontaneously occurring tumors in humans have shown increased uptake of radiolabeled AIB in the tumors relative to normal tissue [Conti, PS et al. (1986), Eur. J. Nucl. Med. 12:353-356; Uehara, H et al. (1997), J. Cereb. Blood Flow Metab. 17:1239-1253]. The N-methyl analog of AIB, N-MeAIB, shows even more selectivity for the A-type amino acid transport system than AIB [Shotwell, M A et al. (1983), Biochim. Biophys. Acta. 737:267-84]. N-MeAIB has been radiolabeled with carbon-11 and is metabolically stable in humans [Någren, K et al. (2000), J. Labelled Cpd. Radiopharm. 43:1013-1021].

Although some of the amino acid analogs mentioned above are currently being evaluated as tumor imaging agents in patients with brain and systemic tumors, there is a continued need for a novel imaging agent which can bind tumor cells or tissues with high specificity and selectivity and can readily be prepared in sufficient quantities for tumor imaging with PET and SPECT. As a candidate compound makes the transition from validation studies in cells in vitro and animal models to application in humans, the synthetic methods employed must be adapted to allow routine, reliable production of the compound in large quantities. Towards this end, the present application discloses a series of novel amino acid compositions, methods of synthesizing and using those compounds for tumor imaging with PET and SPECT.

SUMMARY OF THE INVENTION

The present invention provides novel amino acid compounds useful in detecting and evaluating brain and systemic tumors and other uses. These compounds combine the advantageous properties of 1-amino-cycloalkyl-1-carboxylic acids, namely, their rapid uptake and prolonged retention in tumors with the properties of halogen substituents, including certain useful halogen isotopes such as fluorine-18, iodine-123, iodine-124, iodine-125, iodine-131, bromine-75, bromine-76, bromine-77, bromine-82, astatine-210, astatine-211, and other astatine isotopes. In addition, the compounds can be labeled with technetium and rhenium isotopes using known chelation complexes.

The amino acid compounds of the invention have the following general formula:

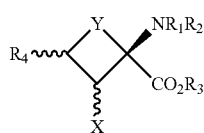

Formula I $Y=(CR_5,R_6)n$; n=1-4, N, O, S, Se

X=halo, haloalkyl, halocycloalkyl, halocycloalkenyl, halocycloalkynyl, haloacyl, haloaryl, haloheteroaryl, haloalkenyl, haloalkynyl, halo=F, Cl, Br, I, At and all isomers including labeled compounds such as F-18, Br-76, I-123, I-124, Tc-99m and Re chelates.

$R_4$, $R_5$ and $R_6$ are independently=H, alkyl, haloalkyl, cycloalkyl, halocycloalkyl, hetero-aryl, aryl, haloaryl, haloheteroaryl, alkenyl, haloalkenyl, alkynyl, haloalkynyl, halo=non-radioactive F, Cl, Br and I.

$R_1$, $R_2$ are independently=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl, Tc-99m and Re chelates.

$R_3$=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl.

The invention also includes compounds represented by the following formula:

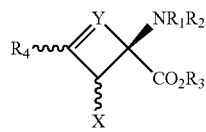

Formula II $Y=(CR_5,R_6)n$; n=1-4, N, O, S, Se

X=halo, haloalkyl, halocycloalkyl, halocycloalkenyl, halocycloalkynyl, haloacyl, haloaryl, haloheteroaryl, haloalkenyl, haloalkynyl, halo=F, Cl, Br, I, At and all isomers including labeled compounds such as F-18, Br-76, I-123, I-124, Tc-99m and Re chelates.

$R_4$, $R_5$ and $R_6$ are independently=H, alkyl, haloalkyl, cycloalkyl, halocycloalkyl, hetero-aryl, aryl, haloaryl, haloheteroaryl, alkenyl, haloalkenyl, alkynyl, haloalkynyl, halo=non-radioactive F, Cl, Br and I.

$R_1$, $R_2$ are independently=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl, Tc-99m and Re chelates.

$R_3$=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl The amino acid compounds of the invention bind target tumor tissues or cells with high specificity and selectivity when administered to a subject in vivo. Preferred amino acid compounds show a target to non-target ratio of at least 2:1, are stable in vivo and substantially localized to target within 1 hour after administration. Because of their high specificity and selectivity for tumor tissues, the inventive compounds can also be used in delivering a therapeutic agent to a given tumor site. Preferred amino acid compounds include (1S*, 2R*)- and (1R*,2S*)-1-amino-2-[$^{18}$F]fluorocyclobutyl-1-carboxylic acid (2-[$^{18}$F]FACBC), (1S*,2R*)- and (1R*,2S*)- and (1S*,2S*)- and (1R*,2R*)1-amino-2-[$^{18}$F]fluoromethyl-cyclobutyl-1-carboxylic acid (2-FMACBC).

Any of F, Cl, Br, I or C in the formulas I and II shown above may be in stable isotopic or radioisotopic form. Particularly useful radioisotopic labels are $^{18}$F, $^{123}$I, $^{125}$I, $^{131}$I, $^{76}$Br, $^{77}$Br and $^{11}$C. The compounds of the invention can also be labeled with technetium and rhenium. Technetium-99m is known to be a useful radionuclide for SPECT imaging. The cyclic amino acids of the invention are joined to a Tc-99m metal cluster through a 4-6 carbon chain which can be saturated or possess a double or triple bond. The Tc-99m metal cluster can be, for example, an alkylthiolato complex, a cytectrene or a hydrazino nicotinamide complex (HYNIC). U.S. Pat. No. 5,817,776 describes various methods of synthesizing [Tc-99m] technetium containing compounds in detail, which is incorporated herein in its entirety.

The inventive compounds labeled with an appropriate radioisotope are useful for tumor imaging with PET and/or SPECT, which can serve as diagnostic purposes or evaluating efficacy of any therapeutic compounds for a given tumor. The inventive method of imaging a tumor comprises (a) introducing into a subject a detectable quantity of a labeled compound of formula I or II or a pharmaceutically acceptable salt, ester or amide thereof; (b) allowing sufficient time for the labeled compound to become associated with tumor tissue; and (c) detecting the labeled compound associated with the tumor with PET or SPECT.

The present invention also provides diagnostic compositions comprising a radiolabeled compound of formula I or II and optionally a pharmaceutically acceptable carrier or diluent. Also within the scope of the invention are pharmaceutical compositions which comprise a compound of formula I or II and optionally a pharmaceutically acceptable carrier or diluent. The pharmaceutical compositions are useful for delivering a therapeutic agent to a specific tumor site in a subject.

Also provided herein are methods of making the compounds of formulas I and II. The synthetic strategy disclosed herein utilizes a cyclic sulfamidate precursor which can be converted to a final product (e.g. 2-FACBC) with greater than 30% decay corrected yield (non-optimized). The high yield of this synthetic strategy is a major advantage which enables sufficient quantities of the compounds of formula I or II, particularly 2-[$^{18}$F]FACBC, available for tumor imaging in contrast to the synthetic strategy for 3-FACBC. The cyclic sulfamidate radiolabeling precursors are more reactive and less moisture-sensitive than trifluoromethane sulfonic ester radiolabeling precursors which are commonly used in the synthesis of anti-and syn-3-[$^{18}$F]FACBC. Furthermore, because the 2-position of the 1-amino-cyclobutyl-1-carboxylic acid is a neopentyl carbon which is not susceptible to SN2 halogen substitution, cyclic sulfamidate radiolabeling precursors are required for F-18 fluoride labeling at the 2-position. Accordingly, the cyclic sulfamidate precursors having the following formula are also within the scope of the invention.

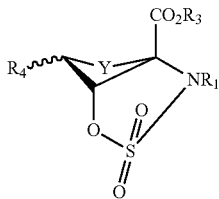

Formula III $Y=(CR_5,R_6)n$; $n=1-4$, N, O, S, Se.

$R_4$, $R_5$ and $R_6$ are independently=H, alkyl, haloalkyl, cycloalkyl, halocycloalkyl, hetero-aryl, aryl, haloaryl, haloheteroaryl, alkenyl, haloalkenyl, alkynyl, haloalkynyl, halo=non-radioactive F, Cl, Br and I.

$R_1$=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl, Tc-99m and Re chelates.

$R_3$=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl.

DETAILED DESCRIPTION OF THE INVENTION

This invention relates to novel amino acid compounds useful for tumor imaging and method of making and using such compounds.

In general the terms and phrases used herein have their art-recognized meaning, which can be found by reference to standard texts, journal references and contexts known to those skilled in the art. The following definitions are provided to clarify their specific use in the context of the invention.

The term "pharmaceutically acceptable salt" as used herein refers to those carboxylate salts or acid addition salts of the compounds of the present invention which are suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "pharmaceutically acceptable salt" as used herein in general refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. See, for example, Berge S. M, et al., Pharmaceutical Salts, *J. Pharm. Sci.* 66:1-19 (1977) which is incorporated herein by reference.

Similarly, the term, "pharmaceutically acceptable carrier," as used herein, is an organic or inorganic composition which serves as a carrier/stabilizer/diluent of the active ingredient of the present invention in a pharmaceutical or diagnostic composition. In certain cases, the pharmaceutically acceptable carriers are salts. Further examples of pharmaceutically acceptable carriers include but are not limited to water, phosphate-buffered saline, saline, pH controlling agents (e.g. acids, bases, buffers), stabilizers such as ascorbic acid, isotonizing agents (e.g. sodium chloride), aqueous solvents, a detergent (ionic and non-ionic) such as polysorbate or TWEEN 80.

The term "alkyl" as used herein by itself or as part of another group refers to a saturated hydrocarbon which may be linear, branched or cyclic of up to 10 carbons, preferably 6 carbons, more preferably 4 carbons, such as methyl, ethyl, propyl, isopropyl, butyl, t-butyl, and isobutyl. The alkyl groups disclosed herein also include optionally substituted alkyl groups where one or more C atoms in backbone are replaced with a heteroatom, one or more H atoms are replaced with halogen or —OH. The term "aryl" as employed herein by itself or as part of another group refers to monocyclic or bicyclic aromatic groups containing from 5 to 12 carbons in the ring portion, preferably 6-10 carbons in the ring portion, such as phenyl, naphthyl or tetrahydronaphthyl. Aryl groups may be substituted with one or more alkyl groups which may be linear, branched or cyclic. Aryl groups may also be substituted at ring positions with substituents that do not significantly detrimentally affect the function of the compound or portion of the compound in which it is found. Substituted aryl groups also include those having heterocyclic aromatic rings in which one or more heteroatoms (e.g., N, O or S, optionally with hydrogens or substituents for proper valence) replace one or more carbons in the ring.

"Acyl" group is a group which includes a —CO— group.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length.

The term "monoalkylamine" as used herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" employed herein by itself or as part of another group refers to chlorine, bromine, fluorine or iodine.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of such heterocyclic groups include piperidinyl, pyrrolyl, pyrrolidinyl, imidazolyl, imidazlinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl, and morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_{1-4}$ alkyl, $C_{2-4}$ aminoalkyl, $C_{1-4}$ halo alkyl, halo benzyl, or $R^a$ and $R^b$ are taken together to form a 5- to 7-member heterocyclic ring optionally having O, S or $NR^c$ in said ring, where $R^c$ is hydrogen or $C_{1-4}$ alkyl.

The compounds of the invention are useful as tumor binding agents and as NMDA receptor-binding ligands, and in radio-isotopic form are especially useful as tracer compounds for tumor imaging techniques, including PET and SPECT imaging. Where X is At, the compounds have utility for radio-therapy. Particularly useful as an imaging agent are those compounds labeled with F-18 since F-18 has a half-life of 110 minutes, which allows sufficient time for incorporation into a radio-labeled tracer, for purification and for administration into a human or animal subject. In addition, facilities more remote from a cyclotron, up to about a 200 mile radius, can make use of F-18 labeled compounds.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Accordingly, the compounds of the invention can be rapidly and efficiently labeled with [$^{123}$I] for use in SPECT analysis as an alternative to PET imaging. Furthermore, because of the fact that the same compound can be labeled with either isotope, it is possible to compare the results obtained by PET and SPECT using the same tracer.

Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the compounds of the invention are now available for use by those skilled in the art, including stable isotope halogen homologs. Astatine can be substituted for other halogen isotopes, [$^{210}$At] emits alpha particles with a half-life of 8.3 h. At-substituted compounds are therefore useful for tumor therapy, where binding is sufficiently tumor-specific.

The invention provides methods for tumor imaging using PET and SPECT. The methods entail administering to a subject (which can be human or animal, for experimental and/or diagnostic purposes) an image-generating amount of a compound of the invention, labeled with the appropriate isotope and then measuring the distribution of the compound by PET if [$^{18}$F] or other positron emitter is employed, or SPECT if [$^{123}$I] or other gamma emitter is employed. An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art without resort to undue experimentation.

It will be understood that compounds of the invention can be labeled with an isotope of any atom or combination of atoms in the structure. While [$^{18}$F], [$^{123}$I] and [$^{125}$I] have been emphasized herein as being particularly useful for PET, SPECT and tracer analysis, other uses are contemplated including those flowing from physiological or pharmacological properties of stable isotope homologs and will be apparent to those skilled in the art.

The compounds of the invention can also be labeled with technetium (Tc) via Tc adducts. Isotopes of Tc, notably $Tc^{99m}$, have been used for tumor imaging. The present invention provides Tc-complexed adducts of compounds of the invention, which are useful for tumor imaging. The adducts are Tc-coordination complexes joined to the cyclic amino acid by a 4-6 carbon chain which can be saturated or possess a double or triple bond. Where a double bond is present, either E (trans) or Z (cis) isomers can be synthesized, and either isomer can be employed. The inventive compounds labeled with Tc are synthesized by incorporating the $^{99m}$Tc isotope as a last step to maximize the useful life of the isotope.

The amino acid compounds of the invention have the following general structure:

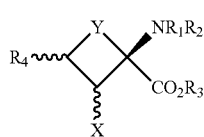

Formula I

Y=(CR$_5$,R$_6$)n; n=1-4, N, O, S, Se

X=halo, haloalkyl, halocycloalkyl, halocycloalkenyl, halocycloalkynyl, haloacyl, haloaryl, haloheteroaryl, haloalkenyl, haloalkynyl, halo=F, Cl, Br, I, At and all isomers including labeled compounds such as F-18, Br-76, I-123, I-124, Tc-99m and Re chelates.

R$_4$, R$_5$ and R$_6$ are independently=H, alkyl, haloalkyl, cycloalkyl, halocycloalkyl, hetero-aryl, aryl, haloaryl, haloheteroaryl, alkenyl, haloalkenyl, alkynyl, haloalkynyl, halo=non-radioactive F, Cl, Br and I.

R$_1$, R$_2$ are independently=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl, Tc-99m and Re chelates.

R$_3$=H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, haloalkynyl.

The amino acid compounds of the above formula are synthesized in specialized, non-standard routes to maximize a useful lifetime for short-lived isotopes (i.e., last step incorporation of isotopes), and to maximize yield and purity, as described below. Scheme 1 exemplifies the synthesis of 2-[$^{18}$F]FACBC, i.e., (S)-(−)-anti-1-amino-2-[$^{18}$F]fluorocyclobutyl-1-carboxylic acid ((S)-(−)-anti-2-[$^{18}$F]FACBC)) and (R)-(+)-anti-1-amino-2-[$^{18}$F]fluorocyclobutyl-1-carboxylic acid ((R)-(+)-anti-2-[$^{18}$F]FACBC)).

The key feature of synthetic scheme 1 is the use of cyclic sulfamidate precursors such as Ia and Ib to enable incorporation of F-18 fluoride onto the 2-position in high radiochemical yield and subsequent efficient conversion into 2-[$^{18}$F]FACBC.

The synthetic strategy outlined in scheme 1 is particularly advantageous in that approximately 2-5 mg of shelf stable cyclic sulfamidate precursor Ia and Ib can provide greater than 30% decay corrected yield of the final product [$^{18}$F] 22 in over 99% radiochemical purity. This is in good contrast with the synthetic strategy used to synthesize anti-3-[$^{18}$F]FACBC (see scheme 2 below) [McConathy et al. (2003) *Journal of Applied Radiation and Isotopes* 28:657-666]. According to the synthetic steps shown in scheme 2, approximately 20 mg of 10 must be used to obtain a reasonable conversion (~24% radiochemical yield (RCY)) of compound 10 into anti-3-[$^{18}$F]FACBC 12. In contrast, the amino acid compounds of the invention can readily be synthesized in sufficient quantities to be used for tumor imaging by the new synthetic strategy shown in schemes 1 and 3

Scheme 1

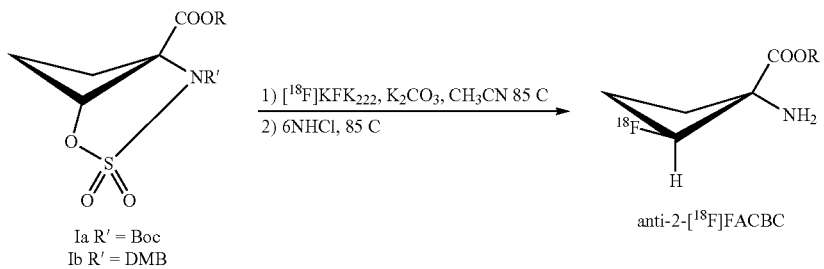

Ia R' = Boc
Ib R' = DMB anti-2-[$^{18}$F]FACBC

Scheme 2

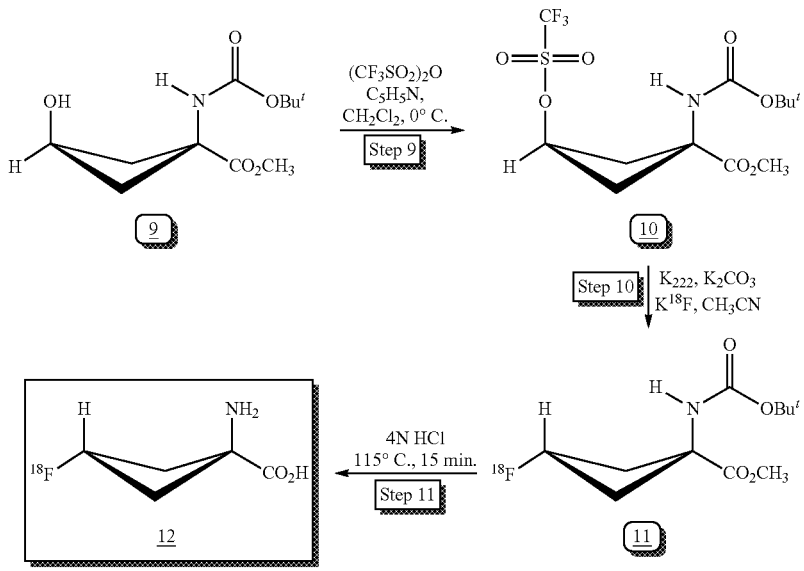

Scheme 2 outlines the synthesis of the anti-3-[$^{18}$F]FACBC labeling precursor, 1-tert-butylcarbamate-3-hydroxy-cyclobutane-1-carboxylic methyl ester (9) and its conversion into anti-[$^{18}$F]FACBC. Treatment of 9 with trifluoromethane sulfonic anhydride/pyridine yielded the cis 1-tert-butylcarbamate-3-trifluoromethanesulfonoxy-cyclobutane-1-carboxylic methyl ester (10). Subsequent treatment of 10 with K$^{18}$F/K$_{222}$ followed by acid hydrolysis yielded anti-[$^{18}$F]FACBC (12). In this synthetic strategy, ~20 mg of 10 must be used to obtain a reasonable conversion (~24% radiochemical yield (RCY)) of 10 into anti-[$^{18}$F]FACBC (12).

Scheme 3 outlines the synthesis of the anti-2-[$^{18}$F]FACBC labeling precursor, syn-4-(bis(4-methoxyphenyl)methyl)-2,3,4-oxathiazabicyclo[3.2.0]heptane-6-carboxylic acid ester 2-oxide (21) and its conversion into anti-2-[$^{18}$F]FACBC. Treatment of 21 with K$^{18}$F/K$_{222}$ followed by acid hydrolysis will yield anti-2-[$^{18}$F]FACBC (22).

Scheme 3

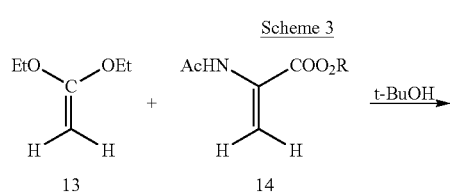

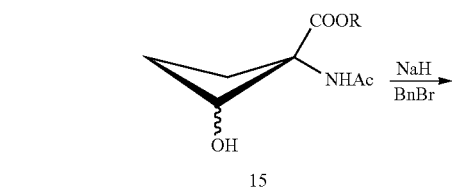

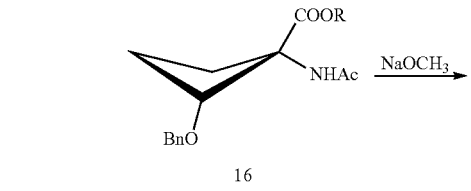

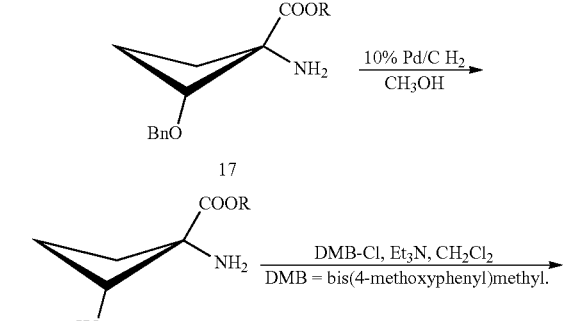

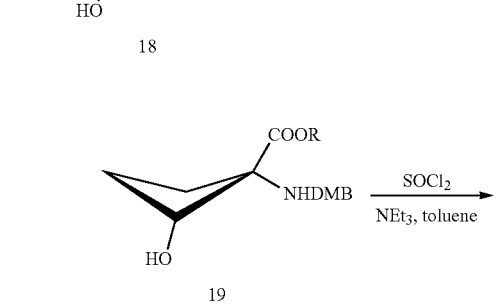

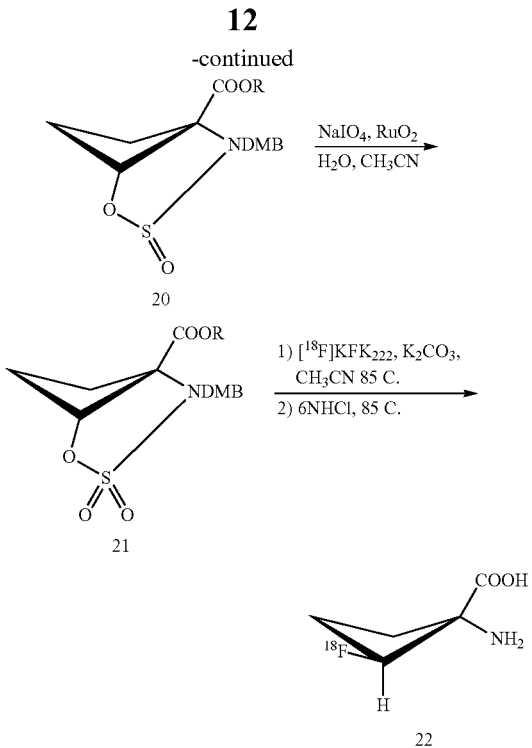

Scheme 4 outlines the synthesis of the anti-2-[$^{18}$F]FACBC labeling precursor syn-4-(tert-butoxycarbonyl)-2,3,4-oxathiazabicyclo[3.2.0]heptane-6-carboxylic acid tert-butyl ester 2,2-dioxide (34) and its conversion into anti-2-[$^{18}$F]FACBC. Treatment of 34 with K$^{18}$F/K$_{222}$ followed by acid hydrolysis will yield anti-2-[$^{18}$F]FACBC (22).

Scheme 4

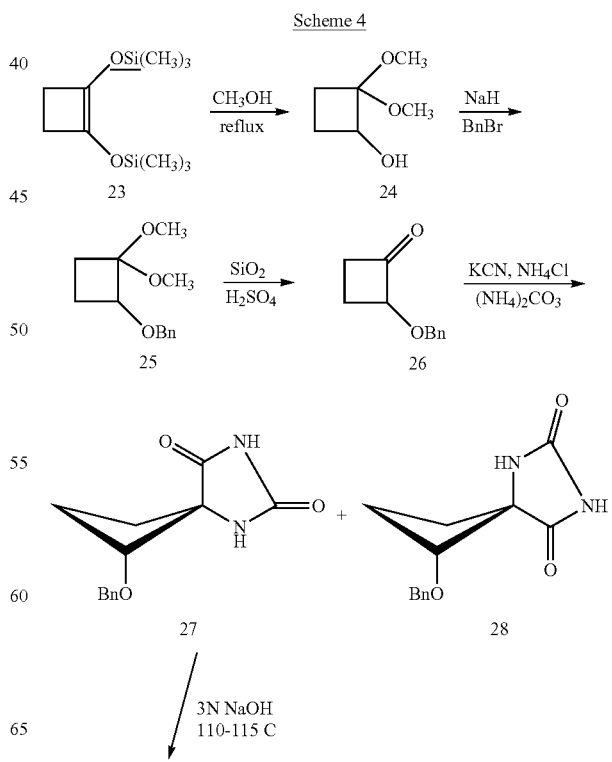

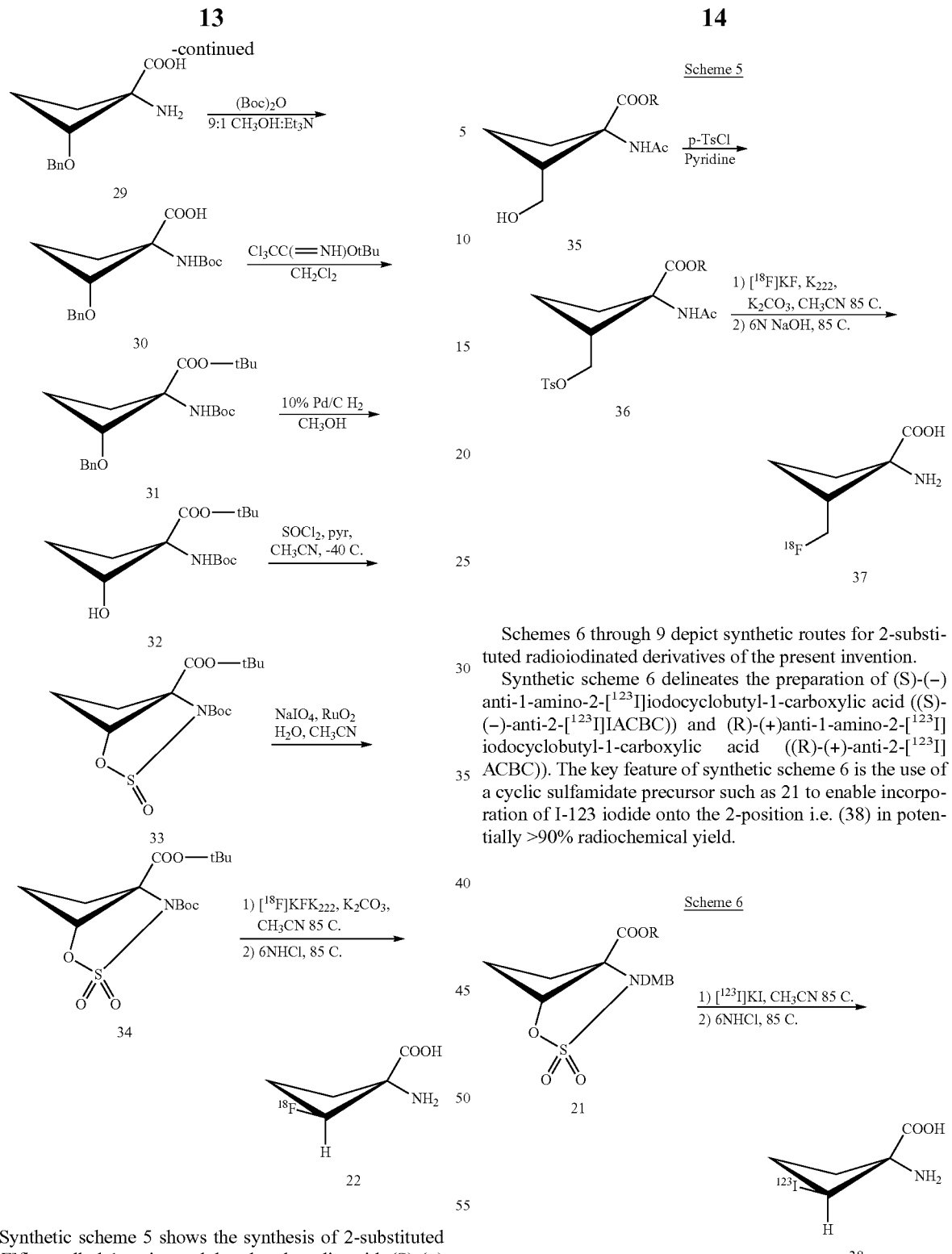

Synthetic scheme 5 shows the synthesis of 2-substituted [$^{18}$F]fluoroalkyl-1-aminocyclobutyl carboxylic acid, (S)-(−)anti-1-amino-2-[$^{18}$F]fluoromethylcyclobutyl-1-carboxylic acid ((S)-(−)-anti-2-[$^{18}$F]FMACBC)) and (R)-(+) anti-1-amino-2-[$^{18}$F]fluoromethylcyclobutyl-1-carboxylic acid ((R)-(+)-anti-2-[$^{18}$F]FMACBC)). The key feature of synthetic scheme 5 is the use of sulfonyl ester precursors such as 36 to enable high radiochemical incorporation of F-18 fluoride onto the 2-methyl group in high radiochemical yield and subsequent efficient conversion of the radiolabeled intermediate [$^{18}$F] 36 into [$^{18}$F]37.

Schemes 6 through 9 depict synthetic routes for 2-substituted radioiodinated derivatives of the present invention.

Synthetic scheme 6 delineates the preparation of (S)-(−) anti-1-amino-2-[$^{123}$I]iodocyclobutyl-1-carboxylic acid ((S)-(−)-anti-2-[$^{123}$I]IACBC)) and (R)-(+)anti-1-amino-2-[$^{123}$I] iodocyclobutyl-1-carboxylic acid ((R)-(+)-anti-2-[$^{123}$I] ACBC)). The key feature of synthetic scheme 6 is the use of a cyclic sulfamidate precursor such as 21 to enable incorporation of I-123 iodide onto the 2-position i.e. (38) in potentially >90% radiochemical yield.

Schemes 7 through 9 depict synthetic routes for 2-substituted radioiodinated iodovinyl derivatives. Iodovinyl derivatives have enhanced in vivo metabolic stability in comparison to iodoalkyl derivatives i.e. 38 due to the attachment of the iodine to a sp2 hydridized carbon. Synthetic scheme 7 shows the preparation of (S)-(−)anti-1-amino-2-[$^{123}$I]iodomethylenecyclobutyl-1-carboxylic acid ((S)-(−)-anti-2-[$^{123}$I] IVACBC)) and (R)-(+)anti-1-amino-2-[$^{123}$I]iodomethylenecyclobutyl-1-carboxylic acid ((R)-(+)-anti-2-[$^{123}$I]IVACBC)). The key feature of synthetic scheme 6 is the use of only 100 μg an organotin precursor such as 42 to enable incorporation of I-123 iodide onto the 2-position in potentially >70% radiochemical yield.

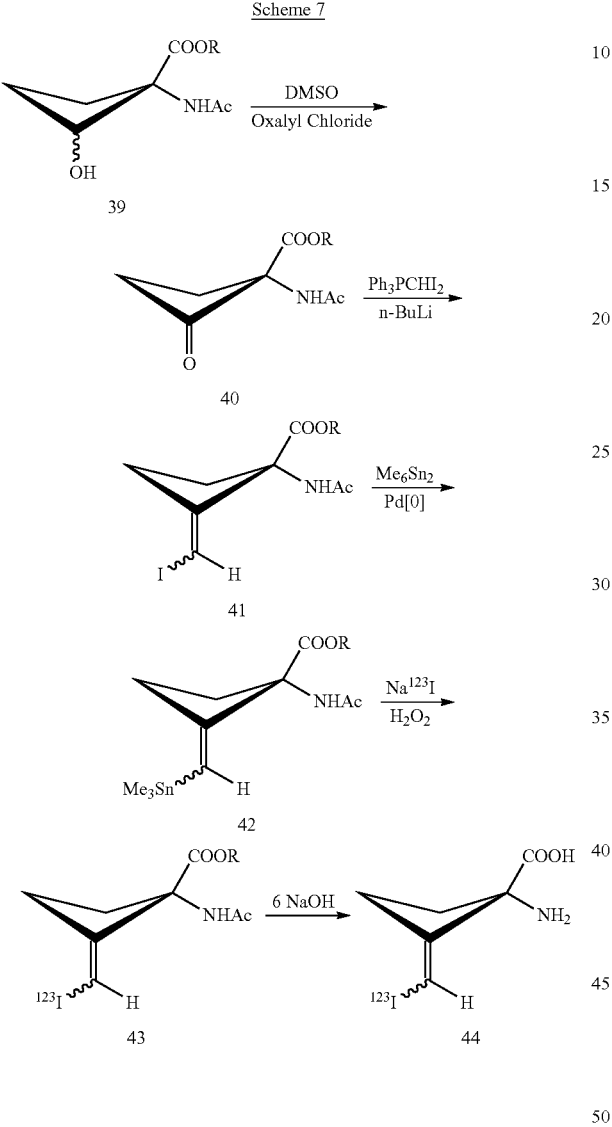

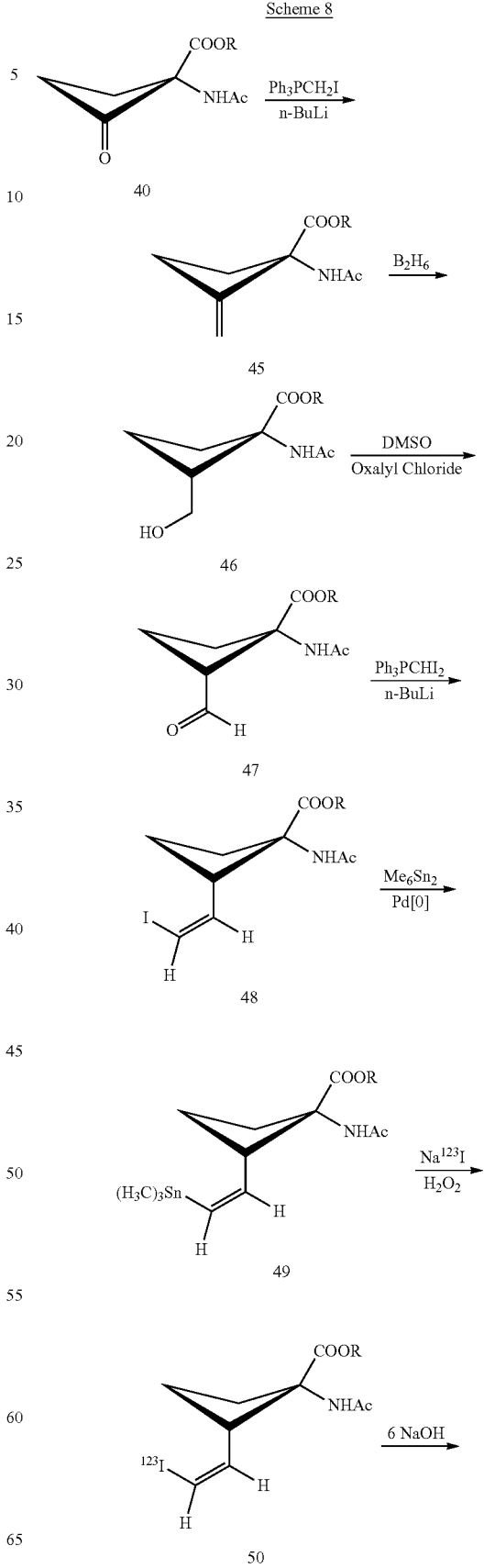

Schemes 8 and 9 depict synthetic routes for 2-substituted radioiodinated iodoethenyl derivatives. Synthetic scheme 8 shows the preparation of cis-(S)-(−)anti-1-amino-2-[$^{123}$I]iodoethenylcyclobutyl-1-carboxylic acid (cis-(S)-(−)-anti-2-[$^{123}$I]IEACBC)) and (cis-(R)-(+)anti-1-amino-2-[$^{123}$I]iodoethenylcyclobutyl-1-carboxylic acid ((R)-(+)-anti-2-[$^{123}$I]IEACBC)). The key feature of synthetic scheme 7 is employing a wittig reagent to obtain the cis confirmation of the iodovinyl moiety. Synthetic scheme 9 shows the preparation of trans-(S)-(−)anti-1-amino-2-[$^{123}$I]iodoethenylcyclobutyl-1-carboxylic acid (trans-(S)-(−)-anti-2-[$^{123}$I]IEACBC)) and (trans-(R)-(−)anti-1-amino-2-[$^{123}$I]iodoethenylcyclobutyl-1-carboxylic acid ((R)-(+)-trans-2-[$^{123}$I]IEACBC)). The key feature of synthetic scheme 9 is employing tri-n-butyltin hydride and AIBN reagents to generate the trans conformation of the iodovinyl moiety.

17
-continued
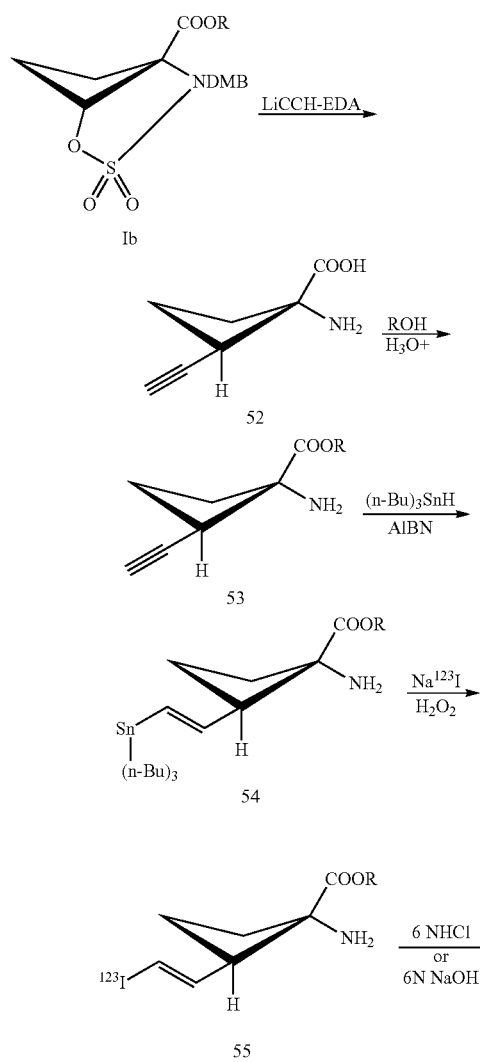
Scheme 9
18
Schemes 10 and 11 depict synthetic routes for 2-substituted Tc-99m derivatives of the present invention.
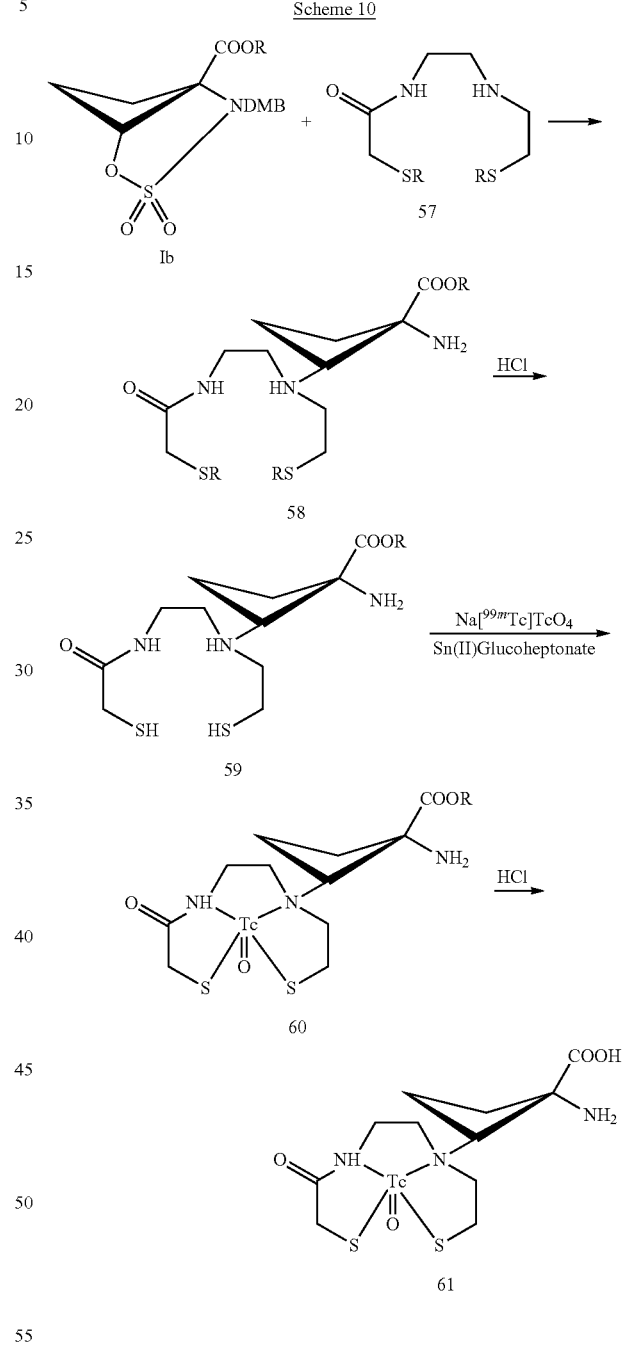
Scheme 10
Scheme 11
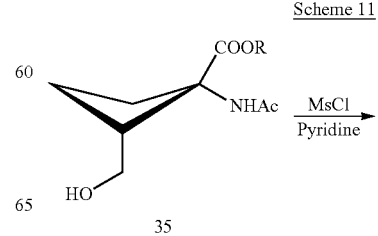

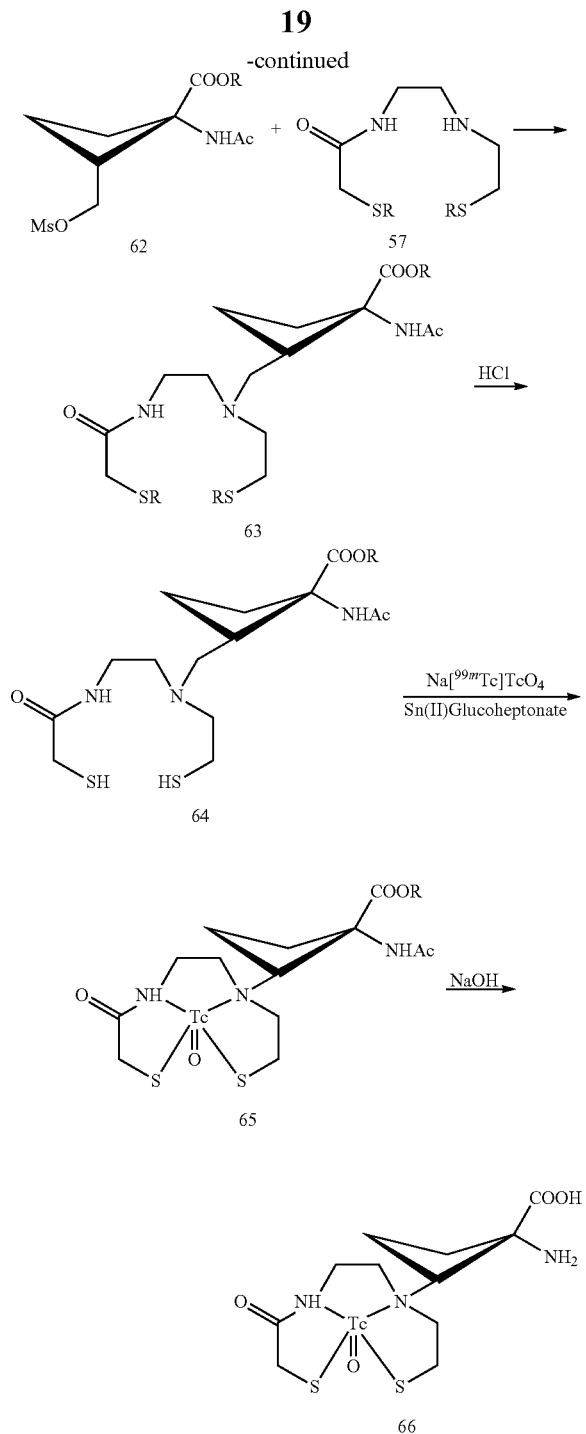

EXAMPLES

The amino acid compounds of the invention synthesized according to the methods disclosed herein are characterized by spectral analyses. Spectral analyses include fast atom bombardment mass spectrometry and $^1$H nuclear magnetic resonance spectrometry analysis. Following purification, all unlabeled agents are analyzed for chemical purity by thin-layer chromatography. All radiolabeled agents are analyzed for radiohomogeneity by thin layer radiochromatographic techniques that are known in the art.

Example 1

Synthesis of 2-FACBC syn-5-(2-benzyloxycyclobutane)hydantoin (27) and anti-5-(2-benzyloxycyclobutane)hydantoin (28)

To a solution of 4 eq of ammonium carbonate (1.97 g, 20.5 mmoles) and 2 eq of ammonium chloride (0.55 g, 10.2 mmoles) in 50 mL of water was added 1 eq of the cyclobutanone 26 (0.9 g, 5.11 mmoles) in 50 mL of ethanol. After stirring at room temperature for 15 minutes, a 1.2 eq portion of potassium cyanide (0.4 g, 6.1 mmoles) was added, and the reaction mix was heated at 70° C. overnight. The solvent was removed under reduced pressure, and the crude cream colored solid was rinsed thoroughly with water to remove salts. The product (0.7 g, 51%) was obtained as a 9:1 mixture of syn:anti isomers.

syn-1-(N-(tert-butoxycarbonyl)amino)-2-benzyloxy-cyclobutane-1-carboxylic acid (30)

A suspension of compounds 27 and 28 (1.26 g, 5.1 mmoles) in 12 mL of 3N sodium hydroxide was heated at 110-115° C. overnight in a sealed stainless steel vessel. After cooling, the reaction mix was neutralized to pH 6-7 with concentrated hydrochloric acid. After evaporation of water under reduced pressure, the resulting solid was extracted with hot ethanol. The combined ethanol extracts were concentrated, and the residue was dissolved in 50 mL of 9:1 methanol:triethylamine. To the solution was added a 1.5 eq portion of di-tert-butyl dicarbonate (1.67 g), and the solution was stirred at room temperature for 72 h. The solvent was removed under reduced pressure, and the crude product was stirred in a mixture of ice-cold 80 mL of ethyl acetate and ice-cold 80 mL of 0.2N hydrochloric acid for five minutes. The organic layer was retained, and the aqueous phase was extracted with 2×80 mL of ice-cold ethyl acetate. The combined organic layers were washed with 3×60 mL of water followed by usual work up. The N-Boc acid 30 (887 mg, 54%) was obtained as a light yellow oil suitable for use in the next step without further purification.

syn-1-(N-(tert-butoxycarbonyl)amino)-2-benzyloxy-cyclobutane-1-carboxylic acid tert-butyl ester (31)

A 2.5 eq portion of tert-butyl 2,2,2-trichloroacetamide (1.5 g, 6.9 mmol) was added to a solution of N-Boc acid 30 (887 mg, 2.76 mmoles) in 10 mL of dichloromethane. After 2 days of stirring, the reaction mixture was filtered, washed with dichloromethane and the filtrate concentrated under reduced pressure, and the crude product was purified via silica gel column chromatography (1:8 ethyl acetate:hexane). The N-Boc tert-butyl ester 31 (634 mg, 61%) was obtained as a colorless oil.

syn-1-(N-(tert-butoxycarbonyl)amino)-3-hydroxycyclobutane-1-carboxylic acid tert-butyl ester (32)

To a solution of 31 (350 mg, 0.93 mmoles) in 10 mL of CH$_3$OH under an argon atmosphere was added 105 mg of 10% Pd/C. The reaction mix was stirred overnight at room temperature under a hydrogen atmosphere. The suspension was then filtered over Celite® and concentrated under reduced pressure purification via silica gel column chromatography (4:1 ethyl acetate:hexane), which provided the alcohol 32 (269 mg, 100%) as a clear oil.

syn-4-(tert-butoxycarbonyl)-2,3,4-oxathiazabicyclo [3.2.0]heptane-6-carboxylic acid tert-butyl ester 2-oxide (33)

A solution of the N-Boc alcohol 32 (48 mg, 0.17 mmol) was added to a cooled (−40° C.) solution of 2.5 eq of thionyl chloride (50 mg, 30 μL) in 1 mL acetonitrile under an argon atmosphere followed by the addition of 5 eq of pyridine (50 mg, 68 μL) in 0.5 mL of acetonitrile. After 10 minutes the cooling bath was removed, and the reaction was continued for 30 minutes. The reaction mix was partitioned between 10 mL of EtOAc and 10 mL of $H_2O$. The aqueous layer was further extracted with 3×10 mL of EtOAc. The organic layers were combined and washed with 20 mL of brine followed by usual work up. Silica gel column chromatography (12.5% EtOAc in hexane) afforded cyclic sulfamidite 33 as a colorless oil (45 mg, 80%).

syn-4-(tert-butoxycarbonyl)-2,3,4-oxathiazabicyclo [3.2.0]heptane-6-carboxylic acid tert-butyl ester 2,2-dioxide (34)

A solution of the sulfamidite 33 (15 mg, 0.045 mmol) in 2 mL of $CH_3CN$ was cooled in an ice bath and treated successively with 1.1 eq of $NaIO_4$ (11 mg), a catalytic amount of $RuO_2.H_2O$ (~0.1 mg) and 1.2 mL of $H_2O$. After 30 minutes of stirring, the ice bath was removed, and the reaction was continued for 20 minutes. The reaction mixture was diluted in 10 mL of EtOAc and washed with 10 mL of saturated $NaHCO_3$ solution. The aqueous layer was extracted with 2×10 mL of EtOAc, and the combined organic layers were washed with 10 mL brine followed by usual work up. The crude product was purified by silica gel column chromatography (25% EtOAc in hexane) to provide the cyclic sulfamidate 34 as a clear oil (15 mg, 96%).

Preparation of (R,S)anti-1-amino-2-[$^{18}$F]fluorocyclobutyl-1-carboxylic acid ((R,S)anti-2-[$^{18}$F] FACBC), 22

To a glass vessel containing 610 mCi of no-carrier-added [$^{18}$F]HF (30 μA, 30 minute bombardment, theoretical specific activity of 1.7 Ci/nmole) in 0.6 mL $H_2O$ containing 5 mg of $K_2CO_3$ was added a 1 mL solution of 5 mg $K_{222}$ Kryptofix in $CH_3CN$. The solvent was removed at 110° C. with argon gas flow, and an additional 1 mL of $CH_3CN$ was added followed by evaporation with argon flow. This drying was repeated a total of 3 times to remove residual $H_2O$. A 2-5 mg portion of the cyclic sulfamidate precursor 34 in 1 mL of dry $CH_3CN$ was added to the vial, and the reaction mix was heated at 90° C. for 10 minutes. The solvent was removed at 115° C. with argon gas flow, and the intermediate product was treated with 0.5 mL of 4N HCl at 110° C. for 10 minutes. The aqueous hydrosylate was allowed to cool for 1 minute and then diluted with approximately 4 mL of sterile saline. The aqueous solution was then transferred to an ion retardation (IR) column assembly consisting of a 7×120 mm bed of AG 11 A8 ion retard resin, a neutral alumina SepPak Plus (preconditioned with 10 mL water) and an HLB Oasis cartridge (preconditioned with 10 mL ethanol then blown dry with 20 mL air), and rinsed with 60 mL of sterile water and then attached to a dose vial. The product [$^{18}$F] 22 was eluted in series through the ion retard resin, the alumina SepPak Plus and the HLB Oasis cartridge. The elution was performed with three successive portions of ~4 mL sterile saline transferred from the glass vial to the IR column assembly. The radiolabeled product eluting from the column assembly passed through a 0.22 μm sterile filter into a dose vial.

In all radiosyntheses, the only peak present on radiometric TLC analysis corresponded to 22 and the radiochemical purity of the product exceeded 99%. The isolated radiochemical yield (30%, non-optimized) was determined using a dose-calibrator (Capintec CRC-712M).

Example 2

Tumor Binding Specificity of Inventive Compounds

The inventive compounds have been evaluated in vitro for tumor binding specificity (i.e. uptake cells) using a variety of tumor cell lines available in the art, along with reference compounds such as Me-AIB and BCH. Detailed description of these assays can be found in Martarello et al. (2002) *Journal of Medicinal Chemistry*, 45:2250-2259 and McConathy et al. (2003) *Nuclear Medicine and Biology*, 30:477-490. These, so called "amino acid uptake studies" are typically carried out with radiolabeled compounds in at least five phenotypically different human tumor cell lines (e.g. A549 lung carcinoma, MB468 breast carcinoma, DU145 prostate carcinoma, SKOV3 ovarian carcinoma, and U87 glial blastoma). These tumor cell lines can be grown either in vitro or in vivo with severe combined immunodeficiency (SCID) mice as a host. The fore-mentioned tumor cell lines are available at the Winship Cancer Institute of Emory University.

For the in vitro amino acid uptake studies, all cells can be grown to monolayer confluency in T-175 culture flasks [Corning, Corning, N.Y.] (approx. $1 \times 10^8$ cells/flask) in Dulbecco's Modified Eagle's Medium (DMEM) [Sigma, St. Louis, Mo.] in a humidified incubator (37° C., 5% $CO_2$/95% air). Media are supplemented with 10% fetal calf serum [Hyclone, Logan, Utah], and antibiotics (10,000 U/ml penicillin and 10 mg/ml streptomycin) (Sigma, St. Louis, Mo.). For tissue culture passage, monolayer cells are detached by gentle trypsinization, resuspended in complete media, and split 1:10 into new T-flasks. Cultures are passaged weekly, and fed fresh media every 2 to 3 days. To initiate tumor growth in SCID mice, $1 \times 10^6$ cells are injected s.c. bilaterally into the flanks (inguinal region) of the recipient animals using a 1 ml syringe with a 27 gauge needle. Ex vivo experiments can be performed with animals containing tumors weighing between 500 mg and 1 g, as estimated by caliper measurement (tumor weight=$(\pi/6)$*abc, where a, b and c are the tumor length, width and height, respectively).

In the in vitro studies the uptake rate of each amino acid compound is measured in each tumor line, as well as the dominant transport mechanisms of each tumor cell line. After trypsinization, cells are resuspended in serum-free media, then counted on a hemocytometer, with viability assessed through Trypan blue staining. Approximately $1 \times 10^7$ cells are exposed to each compound (15 μCi) in 15 ml of amino acid free media for 5, 10, 15, 30 and 60 minutes at 37° C. Cells are then centrifuged at 150×g for 5 minutes, rinsed in 5 ml cold-saline, recentrifuged, resuspended in 3 ml saline, and placed into 12×75 mm glass vials (Fisher, Pittsburgh, Pa.). The vials are placed in a Cobra-II gamma counter (Packard, Meriden, Conn.), with the activity per cell number determined. Inhibition studies determine the dominant transport mechanism (L, A or ASC) for each line [Martarello et al. (2002) supra; McConathy et al. (2003) supra]. For these studies, cells are exposed to the compounds for 30 minutes in amino acid free media containing one of three inhibitors (2-amino-norbornyl- 2-carboxylic acid (BCH), 10 mM; α-(methylamino)-isobutyric acid (MeAIB), 10 mM; and an alanine-serine-cysteine mixture 1:1:1, 10 mM). Saline washes are performed as described above, and the filtered cells radioactivity determined on the gamma counter. Comparisons with the 30 minute control uptake indicate the major transporters used.

The compounds of the invention are further evaluated for their tumor specificity and selectivity in tumor-bearing animal models. One can evaluate and compare the transport, accumulation and tissue distribution of each compound in these in vivo animal studies.

Tissue distribution of the compounds is measured in SCID mice (average weight, 20-25 g) bearing human tumors as follows. The candidate radioligands (20 uCi in 0.4 ml 0.9% NaCl) are injected into the tail vein of tumor-bearing mice. The animals are sacrificed (cervical dislocation) at 5, 30, 60 and 120 minutes post-injection. Tissues (blood, heart, liver, lungs, kidneys, bone, thyroid, muscle, brain and tumor) are excised, rinsed in saline, and blotted dry. The tissues are weighed, placed into 12×75 mm glass vials, the radioactivity determined with a gamma counter, and the percent dose/gram calculated. Total activities of blood and muscle are calculated by assuming that they account for 7% and 40% of the total body mass, respectively.

TABLE 1

% Dose Uptake/0.5e6 Cells of Anti-R,S 2-[$^{18}$F]FACBC In Human Tumor Cells

|  | DU145 | SKOV3 | U87 | A549 | MDA MB 468 |
|---|---|---|---|---|---|
| No inhibitor | 6.40 +/− 0.60 | 2.16 +/− 0.14 | 8.28 +/− 0.45 | 8.89 +/− 0.36 | 7.37 +/− 0.21 |
| BCH | 1.78 +/− 0.20 | 1.74 +/− 0.01 | 2.48 +/− 0.23 | 3.99 +/− 0.39 | 1.67 +/− 0.36 |
| MeAIB | 2.07 +/− 0.26 | 0.75 +/− 0.01 | 5.41 +/− 0.64 | 6.93 +/− 0.20 | 3.02 +/− 0.55 |

TABLE 2

% Dose/g DU145 Prostate Tumor Cells Implanted SC in SCID Mice

|  | blood | heart | lung | liver | pancreas | spleen | kidney | muscle | brain | tumor | bone | Minutes |
|---|---|---|---|---|---|---|---|---|---|---|---|---|
| Average | 2.79 | 2.07 | 3.35 | 2.32 | 29.02 | 4.37 | 6.81 | 0.83 | 0.16 | 2.94 | 1.05 | 15 (n = 5) |
| Std. Dev. | 0.81 | 0.66 | 1.38 | 0.72 | 14.70 | 2.99 | 2.89 | 0.33 | 0.05 | 1.20 | 0.56 |  |
| Average | 1.85 | 1.82 | 2.31 | 2.08 | 29.29 | 4.74 | 4.47 | 0.99 | 0.16 | 3.54 | 1.62 | 30 (n = 5) |
| Std. Dev. | 0.07 | 0.20 | 0.19 | 0.34 | 5.77 | 1.23 | 0.25 | 0.25 | 0.01 | 0.80 | 0.56 |  |
| Average | 0.80 | 1.32 | 1.18 | 1.22 | 15.00 | 2.84 | 1.82 | 1.15 | 0.17 | 2.56 | 2.22 | 60 (n = 5) |
| Std. Dev. | 0.12 | 0.18 | 0.28 | 0.15 | 3.04 | 0.87 | 0.59 | 0.27 | 0.02 | 0.47 | 1.12 |  |
| Average | 0.38 | 0.82 | 0.45 | 0.42 | 5.92 | 0.87 | 0.78 | 0.71 | 0.12 | 1.84 | 0.65 | 120 (n = 5) |
| Std. Dev. | 0.08 | 0.20 | 0.13 | 0.11 | 1.79 | 0.33 | 0.23 | 0.11 | 0.02 | 0.19 | 0.09 |  |

TABLE 3

% Dose/g SKOV3 Ovarian Tumor Cells Implanted SC in SCID Mice

|  | blood | heart | lung | liver | pancreas | spleen | kidney | muscle | brain | tumor | bone | Minutes |
|---|---|---|---|---|---|---|---|---|---|---|---|---|
| Average | 3.01 | 2.37 | 3.96 | 2.62 | 34.27 | 5.00 | 8.70 | 1.14 | 0.18 | 4.89 | 1.40 | 15 (n = 5) |
| Std. Dev. | 0.81 | 0.80 | 1.13 | 1.25 | 17.65 | 2.16 | 3.09 | 0.49 | 0.06 | 2.39 | 0.67 |  |
| Average | 2.22 | 2.16 | 2.65 | 2.49 | 31.88 | 5.22 | 6.12 | 1.21 | 0.21 | 5.56 | 1.46 | 30 (n = 5) |
| Std. Dev. | 0.27 | 0.29 | 0.39 | 0.33 | 7.96 | 1.66 | 0.82 | 0.19 | 0.07 | 1.07 | 0.61 |  |
| Average | 0.94 | 1.40 | 1.26 | 1.28 | 17.57 | 2.57 | 2.27 | 1.03 | 0.15 | 4.53 | 0.91 | 60 (n = 5) |
| Std. Dev. | 0.14 | 0.34 | 0.31 | 0.26 | 4.24 | 1.05 | 0.80 | 0.29 | 0.04 | 1.58 | 0.33 |  |
| Average | 0.53 | 1.00 | 0.68 | 0.67 | 10.42 | 1.51 | 1.37 | 0.65 | 0.16 | 3.39 | 0.94 | 120 (n = 5) |
| Std. Dev. | 0.10 | 0.19 | 0.21 | 0.15 | 3.07 | 0.64 | 0.58 | 0.17 | 0.01 | 0.59 | 0.18 |  |

TABLE 4

% Dose/g A549 Lung Tumor Cells Implanted SC in SCID Mice

|  | blood | heart | lung | liver | pancreas | spleen | kidney | muscle | brain | tumor | bone | Minutes |
|---|---|---|---|---|---|---|---|---|---|---|---|---|
| Average | 3.39 | 2.70 | 4.23 | 3.15 | 48.45 | 7.90 | 10.11 | 1.38 | 0.26 | 5.11 | 2.06 | 15 (n = 5) |
| Std. Dev. | 0.22 | 0.26 | 0.57 | 0.66 | 7.69 | 2.11 | 1.00 | 0.19 | 0.02 | 0.85 | 0.43 |  |
| Average | 2.42 | 2.23 | 3.03 | 2.70 | 44.17 | 5.02 | 5.47 | 1.43 | 0.25 | 4.28 | 1.63 | 30 (n = 5) |
| Std. Dev. | 0.71 | 0.21 | 0.28 | 0.55 | 4.27 | 1.62 | 1.45 | 0.32 | 0.05 | 0.93 | 0.17 |  |
| Average | 1.08 | 1.41 | 1.40 | 1.46 | 20.63 | 2.85 | 2.24 | 0.90 | 0.16 | 3.04 | 1.01 | 60 (n = 5) |
| Std. Dev. | 0.18 | 0.36 | 0.31 | 0.48 | 3.50 | 1.02 | 0.35 | 0.18 | 0.02 | 0.59 | 0.13 |  |
| Average | 0.40 | 0.85 | 0.56 | 0.58 | 9.80 | 1.48 | 1.02 | 0.77 | 0.14 | 2.30 | 0.62 | 120 (n = 4) |
| Std. Dev. | 0.02 | 0.02 | 0.06 | 0.03 | 1.19 | 0.43 | 0.13 | 0.06 | 0.01 | 0.41 | 0.07 |  |

TABLE 5

% Dose/g MB468 Breast Tumor Cells Implanted SC in SCID Mice

|  | blood | heart | lung | liver | pancreas | spleen | kidney | muscle | brain | tumor | bone | Minutes |
|---|---|---|---|---|---|---|---|---|---|---|---|---|
| Average | 3.26 | 2.21 | 4.02 | 2.51 | 36.85 | 4.47 | 8.62 | 1.29 | 0.23 | 2.71 | 1.46 | 15 (n = 5) |
| Std. Dev. | 0.34 | 0.35 | 0.49 | 0.51 | 9.50 | 1.15 | 0.96 | 0.35 | 0.05 | 0.74 | 0.40 |  |
| Average | 2.39 | 1.89 | 2.98 | 2.49 | 35.25 | 4.11 | 6.49 | 1.12 | 0.20 | 2.83 | 1.31 | 30 (n = 5) |
| Std. Dev. | 0.35 | 0.18 | 0.36 | 0.26 | 9.51 | 0.93 | 1.07 | 0.25 | 0.03 | 0.70 | 0.33 |  |
| Average | 1.00 | 1.27 | 1.37 | 1.29 | 19.20 | 3.05 | 2.41 | 1.07 | 0.15 | 2.19 | 0.92 | 60 (n = 5) |
| Std. Dev. | 0.11 | 0.04 | 0.12 | 0.10 | 2.44 | 0.56 | 0.52 | 0.33 | 0.02 | 0.46 | 0.14 |  |
| Average | 0.35 | 0.69 | 0.51 | 0.56 | 7.96 | 1.01 | 0.89 | 0.66 | 0.13 | 1.44 | 0.71 | 120 (n = 5) |
| Std. Dev. | 0.06 | 0.13 | 0.09 | 0.11 | 1.95 | 0.61 | 0.22 | 0.19 | 0.02 | 0.32 | 0.19 |  |

TABLE 6

% Dose/g U87 Glioma Tumor Cells Implanted SC in SCID Mice

|  | blood | heart | lung | liver | pancreas | spleen | kidney | muscle | brain | tumor | bone | Minutes |
|---|---|---|---|---|---|---|---|---|---|---|---|---|
| Average | 3.50 | 2.59 | 4.08 | 3.43 | 49.78 | 6.63 | 9.21 | 1.45 | 0.28 | 6.48 | 2.10 | 15 (n = 5) |
| Std. Dev. | 0.21 | 0.21 | 0.41 | 0.27 | 4.46 | 1.09 | 1.55 | 0.12 | 0.01 | 0.79 | 0.49 |  |
| Average | 2.17 | 2.00 | 2.82 | 2.58 | 41.30 | 5.11 | 5.08 | 1.12 | 0.22 | 5.44 | 1.66 | 30 (n = 5) |
| Std. Dev. | 0.25 | 0.16 | 0.29 | 0.21 | 4.05 | 0.40 | 0.95 | 0.04 | 0.03 | 0.40 | 0.40 |  |
| Average | 0.81 | 1.13 | 1.15 | 1.22 | 17.78 | 3.02 | 2.00 | 1.10 | 0.17 | 3.61 | 1.21 | 60 (n = 5) |
| Std. Dev. | 0.08 | 0.10 | 0.08 | 0.08 | 2.23 | 1.15 | 0.14 | 0.24 | 0.00 | 0.16 | 0.22 |  |
| Average | 0.46 | 0.89 | 0.64 | 0.75 | 10.20 | 1.48 | 1.10 | 0.99 | 0.16 | 2.73 | 1.20 | 120 (n = 5) |
| Std. Dev. | 0.12 | 0.32 | 0.20 | 0.18 | 5.21 | 0.44 | 0.37 | 0.39 | 0.03 | 0.65 | 1.04 |  |

The inventive amino acid compounds have several advantages over [$^{11}$C]-methionine as well as [$^{18}$F]-fluorodeoxyglucose (FDG) for clinical imaging of tumors. These advantages are related to: 1) (S)-(−)-anti-2-[$^{18}$F]FACBC and (R)-(+)-anti-2-[$^{18}$F]FACBC are not metabolized by endogenous enzymes, and radiolabeled metabolites will not confound the interpretation of the images as can be the case with [$^{11}$C] methionine; 2) (S)-(−)-anti-2-[$^{18}$F]FACBC and (R)-(+)-anti-2-[$^{18}$F]FACBC are likely to have better transport, accumulation and tumor imaging characteristics compared to [$^{11}$C] methionine; 3) (S)-(−)-anti-2-[$^{18}$F]FACBC and (R)-(+)-anti-2-[$^{18}$F]FACBC imaging of tumors, will provide different and more clinically useful information than that obtained with [$^{18}$F]-fluoro-2-deoxy-D-glucose (FDG); 4) labeling alicyclic/branched candidate amino acids with [$^{18}$F] instead of [$^{11}$C] will provide substantial logistical and cost-effective benefits for clinical imaging of tumors in a busy nuclear medicine department, due to the longer half-life of [$^{18}$F] ($t_{1/2}$=110 min) compared to [$^{11}$C] ($t_{1/2}$=20 min): and 5) (S)-(−)-anti-2-[$^{18}$F]FACBC and (R)-(+)-anti-2-[$^{18}$F]FACBC have advantages over anti-3-[$^{18}$F]FACBC and syn-3-[$^{18}$F]FACBC because a significantly higher radiochemical yield is possible due to the more reactive and less moisture sensitive cyclic sulfamidate radiolabeling precursors in comparison to more moisture sensitive trifluoromethane sulfonic ester radiolabeling precursors used in the synthesis of anti-3-[$^{18}$F]FACBC.

As exemplified above, the amino acid compounds of the invention have advantageous physiological characteristics (i.e., tumor binding specificity and selectivity, in vivo stability etc). Anti-2-[$^{18}$F]FACBC is an excellent tumor imaging agent using PET based on the following data: 1) In vitro studies in human U87 glioma cells, human DU145 prostate cancer cells, A549 lung cancer cells, SKOV3 ovarian cancer cells, and MB468 breast cancer cells (Table 1) demonstrate that anti-2-[$^{18}$F]FACBC shows high uptake by the type "L" type large-neutral amino acid transport system; 2) In vivo biodistribution studies (Tables 2-6) performed in A549 (lung), DU145 (prostate), SKOV3 (ovary), and MDA MB468 (breast) tumor-bearing SCID mice with anti-2-[$^{18}$F]FACBC injected intravenously showed a rapid and prolonged accumulation of radioactivity in tumors with good tumor uptake (1.4-3.4% dose/g), tumor-to muscle ratio (2-4), tumor-to brain ratio (15-30), tumor-to kidney ratio (1.5-2.7) and tumor-to liver ratio (2.4-4) at 120 min p.i. These data indicate that anti-2-[$^{18}$F]FACBC can provide clinically useful data in both brain and systemic tumors.

The present invention also includes stereoisomers as well as optical isomers, e.g. mixtures of enantiomers as well as individual enantiomers and diastereomers which arise as a consequence of structural asymmetry.

The compounds of formulas I and II may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

When the compounds of the invention are to be used as imaging agents, they must be labeled with suitable radioactive halogen isotopes such as $^{123}$I, $^{131}$I, $^{18}$F, $^{76}$Br, and $^{77}$Br. The radiohalogenated compounds of this invention can easily be provided in kits with materials necessary for imaging a tumor. For example, a kit can contain a final product labeled with an appropriate isotope (e.g. $^{18}$F) ready to use for imaging or an intermediate compound (e.g. compound 1a or 1b in scheme 1) and a label (e.g. K[$^{18}$F]F) with reagents (e.g. solvent, deprotecting agent) such that a final product can be made at the site or time of use.

In the first step of the present method of imaging, a labeled compound of formula I or II is introduced into a tissue or a patient in a detectable quantity. The compound is typically part of a pharmaceutical composition and is administered to the tissue or the patient by methods well known to those skilled in the art. For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In an imaging method of the invention, the labeled compound is introduced into a patient in a detectable quantity and after sufficient time has passed for the compound to become associated with tumor tissues or cells, the labeled compound is detected noninvasively inside the patient. In another embodiment of the invention, a labeled compound of formula I or II is introduced into a patient, sufficient time is allowed for the compound to become associated with tumor tissues, and then a sample of tissue from the patient is removed and the labeled compound in the tissue is detected apart from the patient. Alternatively, a tissue sample is removed from a patient and a labeled compound of formula I or II is introduced into the tissue sample. After a sufficient amount of time for the compound to become bound to tumor tissues, the compound is detected. The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The administration of the labeled compound to a patient can be by a general or local administration route. For example, the labeled compound may be administered to the patient such that it is delivered throughout the body. Alternatively, the labeled compound can be administered to a specific organ or tissue of interest.

Those skilled in the art are familiar with determining the amount of time sufficient for a compound to become associated with a tumor. The amount of time necessary can easily be determined by introducing a detectable amount of a labeled compound of formula I or II into a patient and then detecting the labeled compound at various times after administration.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. PET and SPECT are preferred when the compounds of the invention are used as tumor imaging agents. The label that is introduced into the compound will depend on the detection method desired. For example, if PET is selected as a detection method, the compound must possess a positron-emitting atom, such as $^{11}C$ or $^{18}F$.

The radioactive diagnostic agent should have sufficient radioactivity and radioactivity concentration which can assure reliable diagnosis. For instance, in case of the radioactive metal being technetium-99m, it may be included usually in an amount of 0.1 to 50 mCi in about 0.5 to 5.0 ml at the time of administration. The amount of a compound of formula may be such as sufficient to form a stable chelate compound with the radioactive metal.

The inventive compound as a radioactive diagnostic agent is sufficiently stable, and therefore it may be immediately administered as such or stored until its use. When desired, the radioactive diagnostic agent may contain any additive such as pH controlling agents (e.g., acids, bases, buffers), stabilizers (e.g., ascorbic acid) or isotonizing agents (e.g., sodium chloride). The imaging of a tumor can also be carried out quantatively using the compounds herein so that a therapeutic agent for a given tumor can be evaluated for its efficacy.

Preferred compounds for imaging include a radioisotope such as $^{123}I$, $^{124}I$, $^{125}I$, $^{131}I$, $^{18}F$, $^{76}Br$, $^{77}Br$ or $^{11}C$.

The synthetic schemes described herein represent exemplary syntheses of preferred embodiments of the present invention. However, one of ordinary skill in the art will appreciate that starting materials, reagents, solvents, temperature, solid substrates, synthetic methods, purification methods, analytical methods, and other reaction conditions other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

When a group of substituents is disclosed herein, it is understood that all individual members of that group and all subgroups, including any isomers and enantiomers of the group members, are intended to be individually included. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomers and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Many of the molecules disclosed herein contain one or more ionizable groups [groups from which a proton can be removed (e.g., —COON) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions, those that are appropriate for preparation of salts of this invention for a given application.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of_" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All references cited herein are hereby incorporated by reference to the extent that there is no inconsistency with the disclosure of this specification. In particular, U.S. Pat. Nos. 5,817,776, 5,808,146, and WO 03/093412 are cited herein and incorporated by reference herein to provide examples of the amino cid analogs that can be made using the invention and the detailed synthetic methods. Some references provided herein are incorporated by reference to provide details concerning sources of starting materials, additional starting materials, additional reagents, additional methods of synthesis, additional methods of analysis and additional uses of the invention.

I claim:

1. A method of synthesizing an amino acid analog of the formula

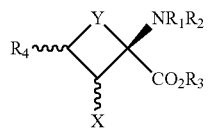

or salt thereof comprising the step of reacting a halogenated compound with a compound of the following formula

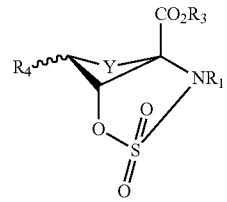

followed by an acid to yield the amino acid analog

R1 is tert-butoxycarbonyl(Boc) or bis(4-methoxyphenyl)methyl in the compound and hydrogen in the amino acid analog;

R2 is hydrogen;

X is selected from the group consisting of halogen, haloalkyl, halocycloalkyl, halocycloalkenyl, halocycloalkynyl, haloacyl, haloaryl, haloheteroaryl, haloalkenyl, haloalkynyl, where halo or halogen in X is selected from the group consisting of F, Cl, Br, I, At, F-18, Br-76, I-123, I-124;

Y is selected from the group consisting of $(CR_5R_6)n$, n=1-4, N, O, S, and Se;

$R_4$, $R_5$ and $R_6$ are independently selected from the group consisting of H, alkyl, haloalkyl, cycloalkyl, halocycloalkyl, heteroaryl, aryl, haloaryl, haloheteroaryl, alkenyl, haloalkenyl, alkynyl, and haloalkynyl, where halo is selected from the group consisting of non-radioactive F, Cl, Br, and I; and $R_3$ is selected from the group consisting of H, alkyl, haloalkyl, cycloalkyl, halocycloalkyl, cycloalkenyl, halocycloalkenyl, cycloalkynyl, halocycloalkynyl, acyl, haloacyl, aryl, haloaryl, heteroaryl, haloheteroaryl, alkenyl, haloalkenyl, alkynyl, and haloalkynyl.

2. The method of claim 1 wherein the amino acid analog is 1-amino-2-[$^{18}$F]fluorocyclobutyl-1-carboxylic acid.

3. The method of claim 1, wherein X is F-18 or I-123.

4. The method of claim 1, wherein Y is $CH_2$.

5. The method of claim 1, wherein R3 is tert-butyl in the compound and H in the amino acid analog.

6. The method of claim 1, wherein R4 is hydrogen.

7. The method of claim 1, wherein the halogenated compound comprises a halogen selected from F-18, Br-76, I-123, and I-124.

8. The method of claim 1, wherein the halogenated compound is a halogen salt.

9. The method of claim 8, wherein the halogen salt is $K^{18}F$, $K^{123}I$, or $Na^{123}I$.

* * * * *